US011324542B2

(12) United States Patent
Ellman et al.

(10) Patent No.: US 11,324,542 B2
(45) Date of Patent: May 10, 2022

(54) RF GENERATOR FOR AN ELECTROSURGICAL INSTRUMENT

(71) Applicant: Elliquence, LLC, Baldwin, NY (US)

(72) Inventors: Alan G Ellman, Hewlett, NY (US); Alfredo Micalizzi, Oceanside, NY (US)

( * ) Notice: Subject to any disclaimer, the term of this patent is extended or adjusted under 35 U.S.C. 154(b) by 274 days.

(21) Appl. No.: 16/101,564

(22) Filed: Aug. 13, 2018

(65) Prior Publication Data

US 2020/0046416 A1 Feb. 13, 2020

(51) Int. Cl.
  *A61B 18/12* (2006.01)
  *A61B 90/00* (2016.01)
  *A61B 90/98* (2016.01)
  *A61B 18/00* (2006.01)

(52) U.S. Cl.
  CPC .......... *A61B 18/1206* (2013.01); *A61B 90/08* (2016.02); *A61B 90/98* (2016.02); *A61B 2018/00589* (2013.01); *A61B 2018/00601* (2013.01); *A61B 2018/00607* (2013.01); *A61B 2018/00642* (2013.01); *A61B 2018/00708* (2013.01); *A61B 2018/00767* (2013.01); *A61B 2018/00779* (2013.01); *A61B 2018/00791* (2013.01); *A61B 2018/00827* (2013.01); *A61B 2018/00875* (2013.01); *A61B 2018/00892* (2013.01); *A61B 2018/00988* (2013.01);
  (Continued)

(58) Field of Classification Search
  CPC ..... A61B 90/08; A61B 90/98; A61B 18/1206; A61B 2090/0803; A61B 2018/00589; A61B 2018/00601; A61B 2018/00607; A61B 2018/00642; A61B 2018/00708; A61B 2018/00767; A61B 2018/00779; A61B 2018/00791; A61B 2018/00827; A61B 2018/00875; A61B 2018/00892; A61B 2018/00988; A61B 2018/1253; A61B 2018/126; A61B 18/1233; A61B 2560/0214; A61B 2017/00221; A61B 2018/1417; A61B 2018/00577; A61B 2018/00702; A61B 2018/00648; A61B 2018/00636; A61B 2018/00654; A61B 2018/00684; A61B 2018/1233; A61B 2018/00696; A61B 2018/0072; A61B 2018/00726; A61B 2018/00732; A61B 2018/00761; A61B 2018/00773; A47L 2501/32; A61N 1/3603

See application file for complete search history.

(56) References Cited

U.S. PATENT DOCUMENTS 5,995,348 A * 11/1999 McCartan .............. H02H 9/025
  361/45
6,238,388 B1 5/2001 Ellman et al.
6,652,514 B2 11/2003 Ellman et al.
(Continued)

OTHER PUBLICATIONS

David J Hay, Electrosurgery, Nov. 21, 2015 (Year: 2015).*
Electrosurgery—BMC proof of date (Year: 2020).*

Primary Examiner — Linda C Dvorak
Assistant Examiner — Nicholas S Borsch

(57) ABSTRACT

A device is provided for generating RF power for an electrosurgical instrument, wherein the circuit provides the electrosurgical current according to a specified set of predefined parameters. The invention further includes at least one read and write RFID that reads information from a RFID tag. The circuit changes the parameters based on the information.

20 Claims, 13 Drawing Sheets

(52) U.S. Cl.
CPC . *A61B 2018/126* (2013.01); *A61B 2018/1253* (2013.01); *A61B 2090/0803* (2016.02)

(56) References Cited

U.S. PATENT DOCUMENTS

| | | | |
|---|---|---|---|
| 7,674,261 B2 | 3/2010 | Garito et al. | |
| 7,832,258 B2 * | 11/2010 | Mudge | B05B 15/18 73/86 |
| 8,998,891 B2 * | 4/2015 | Garito | A61B 18/12 606/34 |
| 2003/0050633 A1 * | 3/2003 | Ellman | A61B 18/12 606/37 |
| 2008/0030345 A1 * | 2/2008 | Austin | A61B 90/98 340/572.8 |
| 2009/0281464 A1 * | 11/2009 | Cioanta | A61B 90/96 601/2 |
| 2011/0301607 A1 * | 12/2011 | Couture | A61B 18/1206 606/52 |
| 2013/0267947 A1 * | 10/2013 | Orszulak | A61B 18/1233 606/41 |
| 2013/0304061 A1 * | 11/2013 | Chang | A61B 18/1206 606/41 |
| 2014/0276768 A1 * | 9/2014 | Juergens | A61B 18/1233 606/34 |
| 2016/0151107 A1 * | 6/2016 | Wham | A61B 18/1206 700/287 |
| 2018/0132850 A1 * | 5/2018 | Leimbach | A61B 90/98 |
| 2019/0207911 A1 * | 7/2019 | Wiener | H04L 63/0428 |

* cited by examiner

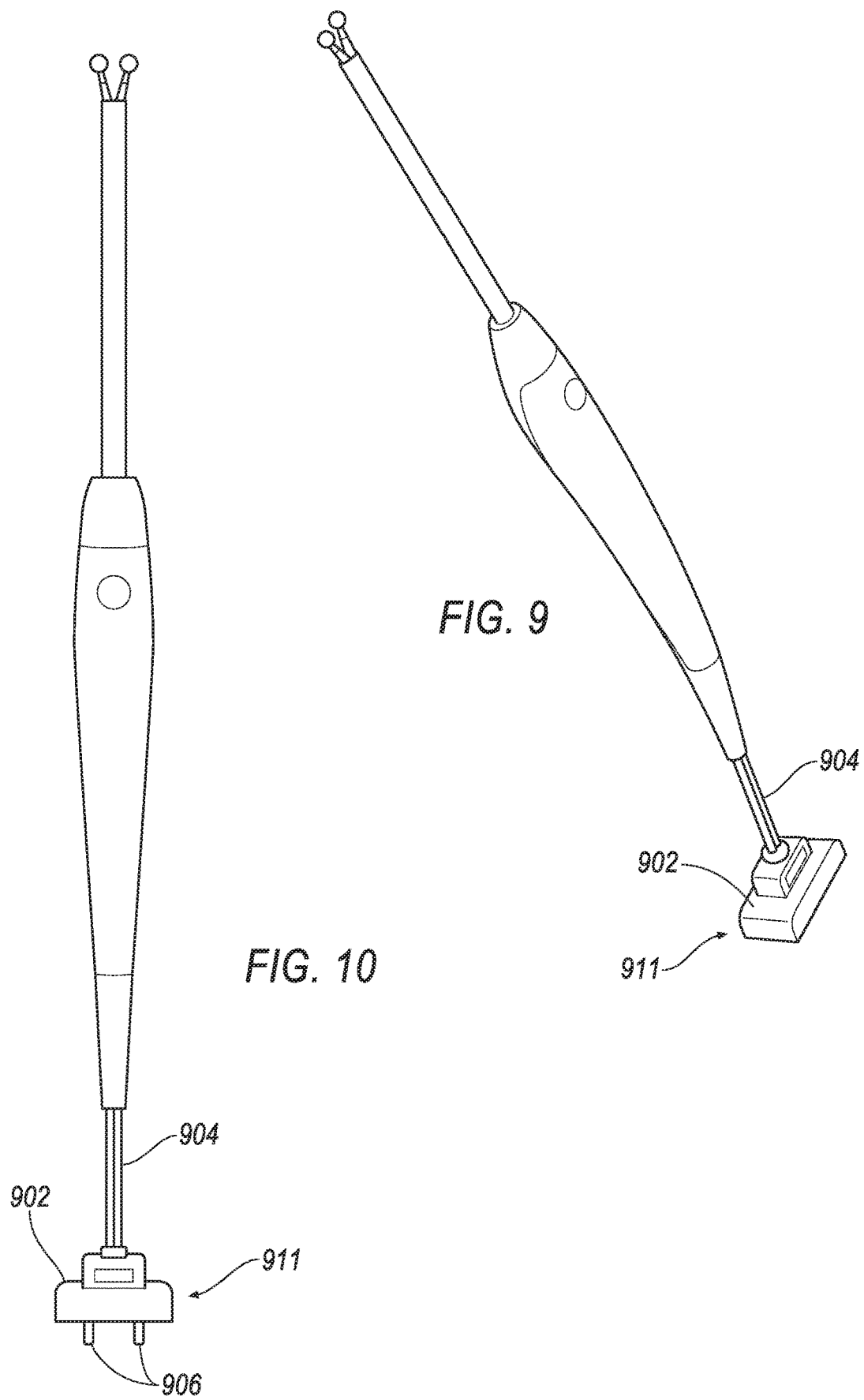

RF GENERATOR FOR AN ELECTROSURGICAL INSTRUMENT

CROSS REFERENCE TO RELATED APPLICATIONS

The present application is a Continuation in Part of a Utility application Ser. No. 15/291,406 entitled RF Generator For An Electrosurgical Instrument, which further claims priority to provisional application No. 62/247,663 for a RF GENERATOR FOR AN ELECTROSURGICAL INSTRUMENT, the entirety of the aforementioned applications are hereby incorporated by reference.

FIELD OF INVENTION

The present invention relates to an RF generator and more specifically, the present invention relates to an RF generator for performing surgical procedures utilizing an electrosurgical instrument.

BACKGROUND

Electrosurgical instruments are well known and widely used in the medical, dental, and veterinary fields. Such instruments may generate electrical currents in the RF spectrum which are used to deliver power to hand-held surgical tools incorporating an electrode component and are used to perform surgical procedures such as tissue cutting, coagulation, hemostasis and other electrosurgical applications. An example electrosurgical instrument is described in U.S. Pat. No. 8,998,891 whose full contents are hereby incorporated by reference.

Electrosurgical instruments may include a unit for generating RF power which is delivered to hand-held surgical tools to activate an incorporated electrode or electrodes used to perform electrosurgical procedures. Electrosurgical instruments commonly utilize multiple modes of power delivery including monopolar and bipolar power delivery modes which are used to operate a monopolar or a bipolar handpiece. A monopolar handpiece or apparatus may incorporate a monopolar electrode which engages surgical tissue with a neutral plate return positioned on a patient's body. A bipolar apparatus may incorporate a pair of electrodes both of which engage surgical tissue into an electrosurgical circuit. Different surgical handpieces are designed and stylized for a particular mode of power delivery such as a handpiece providing a monopolar needle electrode or handpiece providing bipolar electrode forceps.

A console-type receptacle or console unit may be used to house a circuitry for RF power generation and to provide input and output connections from such circuitry to a variety of external devices including a power supply and a number of hand-held surgical tools. A console unit may include interactive display and input panels for user-operation of the electrosurgical instrument. Input panels provide switches, buttons, touch screens, IR controls and the like to allow a user to select and input the operating conditions in order to activate the electrosurgical tool for a specific surgical operation or procedure. Activation of a particular handpiece may be directed by a user from the interactive input panels. Alternately, handpiece activation means such as a connected footswitch or a finger switch in the handpiece may be used to electrically activate the surgical tool to receive RF power for use in a surgical procedure.

SUMMARY OF THE INVENTION

A device for generating RF power for an electrosurgical instrument has a controller programmed to generate an electrical signal having an oscillating waveform and to modulate said oscillating waveform between a plurality of ON and OFF states to create discrete packets of the waveform in the plurality of the ON states. The device further has an amplifier in communication with said electrical waveform that amplifies said waveform to create an output signal and an electrosurgical connector configured to receive an electrosurgical instrument and to pass said electrical signal to said electrosurgical instrument. The oscillating waveform has a frequency in the RF spectrum and the plurality of ON and OFF states creating the discrete packets has a frequency slower than that of the oscillating waveform.

The controller of the device is configured to modulate each of the discrete packets between SUB ON and SUB OFF states to form a plurality of sub-discrete packets of the waveform. The plurality of SUB ON and SUB OFF states creating the sub-discrete packets has a frequency which is less than the frequency of the oscillating waveform and greater than the frequency of the discrete packets.

The controller of the device is configured to modulate each of the sub-discrete packets between a second level SUB ON and a second level SUB OFF states to form a plurality of second level sub-discrete packets within each of the sub-discrete packets. The plurality of second level SUB ON and second level SUB OFF states creating the second level sub-discrete packets has a frequency which is less than the frequency of the oscillating waveform and greater than the frequency of the sub-discrete packets.

The discrete packets and discrete sub-packets of the waveform are formed within a modulation envelope and the modulation envelope may have a variety of shapes including rectangular, triangular, saw tooth, non-uniform, stair-step, ascending, descending and oval.

The oscillating waveform of the device is an alternating sine wave which fluctuates between a first minimum voltage level and first maximum voltage level. The oscillating waveform has a frequency between 200 kHz and 4 MHz. The plurality of ON and OFF states creating the discrete packets has a frequency between 37 Hz and 75 Hz. The plurality of SUB ON and SUB OFF states creating the sub-discrete packets has a frequency between 10.7 kHz to 14.5 kHz or 3 kHz to 19 kHz. The plurality of second level SUB ON and second level SUB OFF states creating the second level sub-discrete packets has a frequency of 2 MHz and a duty cycle of 50%. The power of the electrical signal output to the electrosurgical instrument is in a range of between 40 watts and 200 watts.

The device for generating RF power further includes at least one at least one sensing device disposed within the electrosurgical tool and a feedback circuit in electrical connection with the sensing device. The sensing device is configured to collect electrical power usage signals from the electrical tool that represents an amount of power being distributed to an operative field by the electrosurgical instrument; and the feedback circuit configured to adjust the output signal to the electrosurgical instrument to keep the amount of power at the operative field substantially constant. The sensing device collects electrical power usage signals, for example impedance, voltage, current and temperature, and the feedback circuit comprises an algorithm utilizing the impedance, voltage, current and temperature signals to adjust the voltage supply input to the amplifier. The electrosurgical tool comprises a monopolar or a bipolar handpiece.

In another aspect of the invention, a device is provided for generating RF power for an electrosurgical instrument, wherein the circuit provides the electrosurgical current according to a specified set of predefined parameters. The invention further includes at least one read and write RFID that reads information from a RFID tag. The circuit changes the parameters based on the information.

BRIEF DESCRIPTION OF THE DRAWINGS

FIG. 9 illustrates a perspective view of an electrosurgical headpiece used in connection with an RF Generator for an Electrosurgical Instrument according to an aspect of the current invention;

FIG. 10 illustrates a perspective view of an electrosurgical headpiece used in connection with an RF Generator for an Electrosurgical Instrument according to an aspect of the current invention;

DETAILED DESCRIPTION

U.S. Pat. No. 7,674,261 B2 entitled Electrosurgical Instrument with Enhanced Capability, U.S. Pat. No. 8,998,891 entitled Tri-Frequency Electrosurgical Instrument, U.S. Pat. No. 6,652,514 B2 entitled Intelligent Selection System for Electrosurgical Instrument, and U.S. Pat. No. 6,238,288 B1 entitled Low-Voltage Electrosurgical Apparatus, the entirety of all of the aforementioned patents are hereby incorporated by reference.

The circuitry used to generate RF power for a conventional electrosurgical instrument is inflexible in that it typically requires a number of bulky, discrete components which are used to generate a limited number of waveforms at a limited number of frequencies. Additionally, the modulation stage of conventional RF power generating circuitry for this application is limited and may only include one modulation of the carrier wave so that only a single, coarse modulation treatment is available to adjust the electrical waveform to match a desired output power target.

It is desirable for an electrode or electrodes of an electrosurgical instrument to direct and to deliver a surgical affect to a portion of tissue using a predictable output power level and stable power usage. As the operative tissue is typically a part of the electrical circuit of an electrosurgical tool, changes in the tissue composition and factors specific to the electrodes can cause changes to the load resistance in the RF power circuitry. A sudden low impedance condition in the RF power generating circuit may impact power usage at an operative site creating undesirable or unpredictable heat transfers or losses to the surgical tissue. Factors such as including temperature, tissue density, fluid at an operative site, gradient of tissue types at the operative site, as well as other factors may impact load resistance. These factors create a changing electrical power load on the electrode which causes the power level to fluctuate creating potentially unwanted variation in operating conditions on the operative tissues. Lacking any feature to compensate for this varying power load, conventional RF power generating circuitry is subject to undesirable power usage variation resulting in undesirable surgical results.

Figure 1:
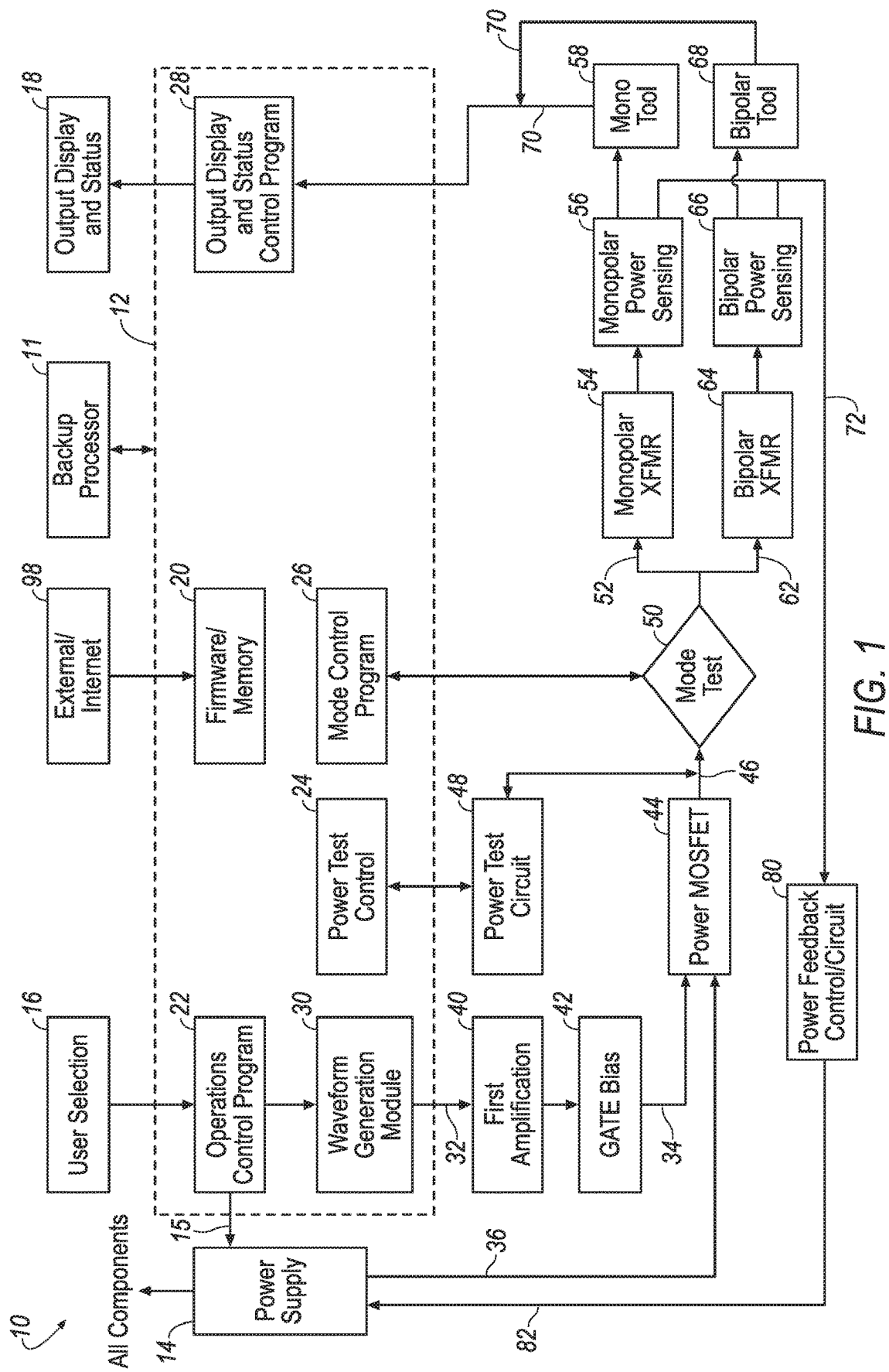
FIG. 1 illustrates a block diagram of a circuit for an electrosurgical instrument according to one aspect of the current invention.

One form of RF circuitry 10 according to one aspect of the current invention is illustrated in the block diagram of FIG. 1. RF circuitry 10 includes a lightweight and versatile power supply 14 with a power entry module capable of auto-sensing input power settings preferably in the range of 90 to 264 volts. Components of RF circuitry 10 may be mounted in a conventional manner on circuit boards with interconnecting conductors providing electrical interconnection between components and power supply 14. Power supply 14 provides a range of voltage outputs, preferably in the range of 3 V to 48V and includes internal circuitry for AC to DC power conversion used, for example, for converting AC power low voltage DC power for electrical components. In particular, power supply 14 can be configured to supply any combination of 5V, 12V, 24V or 48V output modes and a power output of up to 600 watts. Power supply 14 provides electrical power to all components in RF circuitry 10, although other sources such as a battery source for a wireless component or battery backup may also be utilized as well as a component of RF circuitry 10.

Power supply 14 provides electrical power to a controller or a main microprocessor which is represented by dashed block 12 of FIG. 1. Main processor 12 is a programmable device utilized to control the operation of RF circuitry 10. Included within dashed block of main processor 12 are blocks which represent a subset of the functionality performed by main processor 12 in the generation of RF waveforms as will be described.

In one embodiment of the invention, main processor 12 comprises a high speed microprocessor. This exemplary microprocessor includes features such as programmable firmware and memory components 20 which can be updated by way of external/internet connection 98. One skilled in the art will understand that other processors than the aforementioned processor may be employed. Programmable firmware and memory components 20 may be advantageously updated via external/internet connection 98 to provide new or optimized programs and other features used for generating RF waveforms for powering an electrosurgical instrument. External/internet connection 98 may utilize a USB port or IR wireless connection provided in a console unit used to house RF circuitry 10. External/internet connection 98 may also comprise an external device such as a flash drive or hard drive or other device in communication with main processor 12.

In one example, RF circuitry 10 includes a backup or a slave processor 11 which is in continuous communication with main processor 12 for the purpose of providing additional computation power, memory, as well as a backup processor for system safety. Backup processor 11 may include some of the same features as main processor 12 such as a high speed internal precision oscillator with clock speeds up to 24.5 MHz. Backup processor 11 may be used to reinforce the functionality of main processor 12 and provide a backup processor in the occurrence of a failure of main processor 12. A portion of the executable processes required by main processor 12 may be handed off to backup processor 11 to increase overall processing speeds. Backup processor 11 may include an expanded interrupt handler in connection with alarm and power supply components of RF circuitry 10 for safety features of an electrosurgical instrument utilizing the current invention.

Firmware and memory components 20 are programmable to create and store any number of control programs used to direct operation of RF circuitry 10. In one example of the current invention, operations control program 22 is programmed to provide parametric settings and executable commands for generating and modulating waveform signals which are activated with a selected surgical mode of operation of an electrosurgical instrument. A surgical mode of operation may be provided by a user of the electrosurgical instrument by way of user selection 16. Input from user selection 16 is used to signal main processor 12 to activate specific programs for a particular waveform using operations control program 22. Operations control program 22 is included in main processor 12 and is updatable via firmware/memory components 20. User selection 16 includes signals from a number of hardware features including, but not limited to, input from a handpiece switch of an electrosurgical handpiece, input from a footswitch, input from a display panel of a connected console, a wireless signal using Bluetooth or other technology, or a combination of the above. User selection 16 is input into operations control program 22 to determine settings for operational parameters such as waveform frequency, target power setting, selection of monopolar or bipolar mode power delivery, and selection of a surgical mode of operation such as CUT, CUT/COAG, COAG, HEMO, BIPOLAR HEMO, BIPOLAR TURBO, FULGURATE, and other modes of operation. Settings for these operational parameters are controlled by operations control program 22 which feeds the settings to waveform generation module 30 and power supply 14. In another example of the current invention, operational control program 22 stores "prior use" settings of operational parameter settings which were used in the previous or last operation of RF circuitry 10. Operational control program 22 stores and maintains default settings for operational parameters for each surgical mode of operation. In some cases, it is preferable to use prior use settings or default settings for the operation of an electrosurgical instrument incorporating RF circuitry 10. Various examples of methods for user selection of an operational mode for an electrosurgical instrument is described in the aforementioned patents incorporated in their entirety for reference.

RF circuitry 10 includes waveform generation module 30 to provide RF power at a customizable and controllable output power level to an electrosurgical tool such as monopolar handpiece 58 or bipolar handpiece 68 or other surgical tool to perform a selected surgical mode of operation. Waveform generation module 30 utilizes exemplary features of main processor 12 such as programmable and general purpose counter and timer arrays with capture and compare modules, an integrated watchdog timer clock, a wide variety of both digital and analog functionality including an integrated Digital-to-Analog convertor, an integrated built-in Voltage Reference, as well as other features to generate electrical waveform signals in the RF spectrum. In one example, main processor 12 has a maximum clock speed of 24,000 MHz and is capable of executing instructions at a much higher rate than some electrosurgical units currently in operation.

In an example of RF circuitry 10, waveform generation module 30 of main processor 12 has the capability to provide multiple waveforms with different output frequencies which are adjustable and are in the range of 200 KHz to 4.00 MHz. It should be understood that while a particular frequency may be described for use in the current invention, RF circuitry 10 may be utilized to provide any frequency within the capabilities of main processor 12.

In one preferred mode of operation, waveform generation module 30 outputs a waveform which is a 4 MHz sine wave and may be utilized to perform a particular surgical mode of operation with a monopolar handpiece 58. In this example, output waveform 32 produced from waveform generation module 30 is a continuous waveform. The continuous waveform may be modulated to customize the waveform for another mode of surgical operation. The waveform generation module 30 of the present invention generates a wide range of waveform types and at a wide range of frequencies utilized by various surgical modes of operation for an electrosurgical instrument. Generation of electrical waveform signals is discussed in further detail with FIG. 3A through FIG. 5E.

Output waveform 32 is an AC signal which is first amplified with 1st waveform amplification 40 for which the output is then provided as a gate voltage to gate bias 42 for power MOSFET 44. Although other amplification means may be employed by the present invention, the power MOSFET 44 provides amplification via a gate voltage to provide consistency between the input and amplified waveform. First amplification 40 of output waveform 32 may be accomplished using components such as a preamp, a standard driver, and/or a transformer. The transformer, in connection with power amplifier MOSFET 44, allows power MOSFET 44 to oscillate and to step up a voltage signal from a lower voltage to a much higher voltage.

The output waveform is input as the gate bias 42 to the power MOSFET 44 which gates the voltage provided by the power supply 14 to result in the output waveform 32 amplified to the voltage of the power supply 14. The output of power MOSFET 44 is monitored for safety's sake by power test circuit 48 under the control of power test control 24 of main processor 12.

It should be understood that other power amplification devices may be utilized. RF circuitry 10 utilizes power supply 14 to provide input power 36 across the drain circuit of power MOSFET 44 while output waveform 32 provides gate bias 42 for operating power MOSFET 44 in the linear operating region to amplify waveform 32 and to generate output RF power 46 to operate a surgical tool such as a bipolar handpiece 68 or monopolar handpiece 58 of an electrosurgical instrument.

Output RF power 46 is fed to mode tester circuit 50 which is controlled by mode control program 26 of main processor 12. Mode tester circuit 50 utilizes settings from mode control program 26 to verify which power delivery mode and, therefore, which type of handpiece was selected for a surgical mode of operation. Mode tester circuit 50 confirms that output RF power 46 is appropriately directed to monopolar transformer 54 for a monopolar mode of operation, or to bipolar transformer 64 for a bipolar mode of operation. In a method to determine the appropriate power mode, mode control program 26 receives input from user selection 16 of a monopolar or a bipolar mode of operation. Mode control program 26 may also access default operational settings or the operational settings of a prior use stored in in operation control programs 22 of main processor 12 to determine which mode of electrosurgical handpiece is appropriate. Mode tester circuit 50 provides a safety feature to ensure that output power 46 will match and activate the selected surgical handpiece or electrosurgical tool 58 and 68. In another embodiment of the invention, mode tester circuit 50 and mode control program 26 are combined into one electrical circuitry unit which includes the capability test for a selected mode of operation and to confirm that the appropriate electrosurgical handpiece receives output RF power 46 for that selected mode of operation. In another embodiment, mode tester circuit 50 is configured to test and verify the power delivery mode for other types of electrosurgical tools which are not handheld tools.

In an example of the current invention of FIG. 1, an electrosurgical handpiece may include a power sensing module for monitoring power usage during an electrosurgical operation. Monopolar power sensor module 56 and bipolar sensing module 66 are configured to measure electrical and physical characteristics from a strategic position on a handpiece during a surgical procedure, for example at point close to the end of the handpiece 58 or 68 or incorporated into a portion of handpiece 58 or 68 to monitor the power load at the site of the electrosurgical procedure. In one example, if constant current is assumed, the voltage can be adjusted at the input power supply 14 to compensate for changing resistances (say for moist or dry tissue for example) to provide a constant power or wattage to a probe or electrode in the handpiece at the site of surgical operative tissue. Monopolar power sensing module 56 and bipolar sensing module 66 are connected to power feedback control circuit 80 by way of connector 72 to provide a feedback of power usage to power supply 14. Power sensing modules 56 and 66 may include electrical circuitry or sensors positioned within a monopolar or bipolar handpiece, positioned externally adjacent to the handpiece, or positioned in multiple locations in order to detect characteristics such as current, voltage, impedance, temperature and other electrical or physical characteristics reflecting the load resistance and power usage at an operational site. Power sensing modules 56 and 66 may also detect temperature, humidity, and other physical conditions at the site of a surgical operation utilizing RF power circuitry 10. Sensors and circuitry associated with power sensing modules 56 and 66 may be incorporated in a surgical handpiece or comprise a component external to a surgical handpiece. The data collected by these circuits and/or sensors are sent to power feedback control circuit 80 via connector 72 which may be a hardwire connector or a wireless connection.

Power feedback control circuit 80 may be an independent component or an independent set of components in communication with power supply 14 by way of connector 82. Power feedback control circuit 80 may also be comprised of firmware and memory components in main processor 12. Power feedback control circuit 80 provides instantaneous power adjustments to maintain a desired power load being used by an electrosurgical handpiece or other surgical tool. In one example, an electrode or set of electrodes are incorporated in an electrosurgical handpiece to direct RF power to a specific portion of surgical tissue or surgical body part. Power feedback control circuit 80 is programmed to provide real time analysis of power usage from power sensing modules 56 and 66, and execute algorithms to determine power supply adjustments, and to signal power supply 14 to make adjustments in the delivery of electrical power from power supply 14 to power amplifier MOSFET 44. Power input 36 to power amplifier MOSFET 44 is thereby adjusted to provide a desired output power 46.

Figure 2:
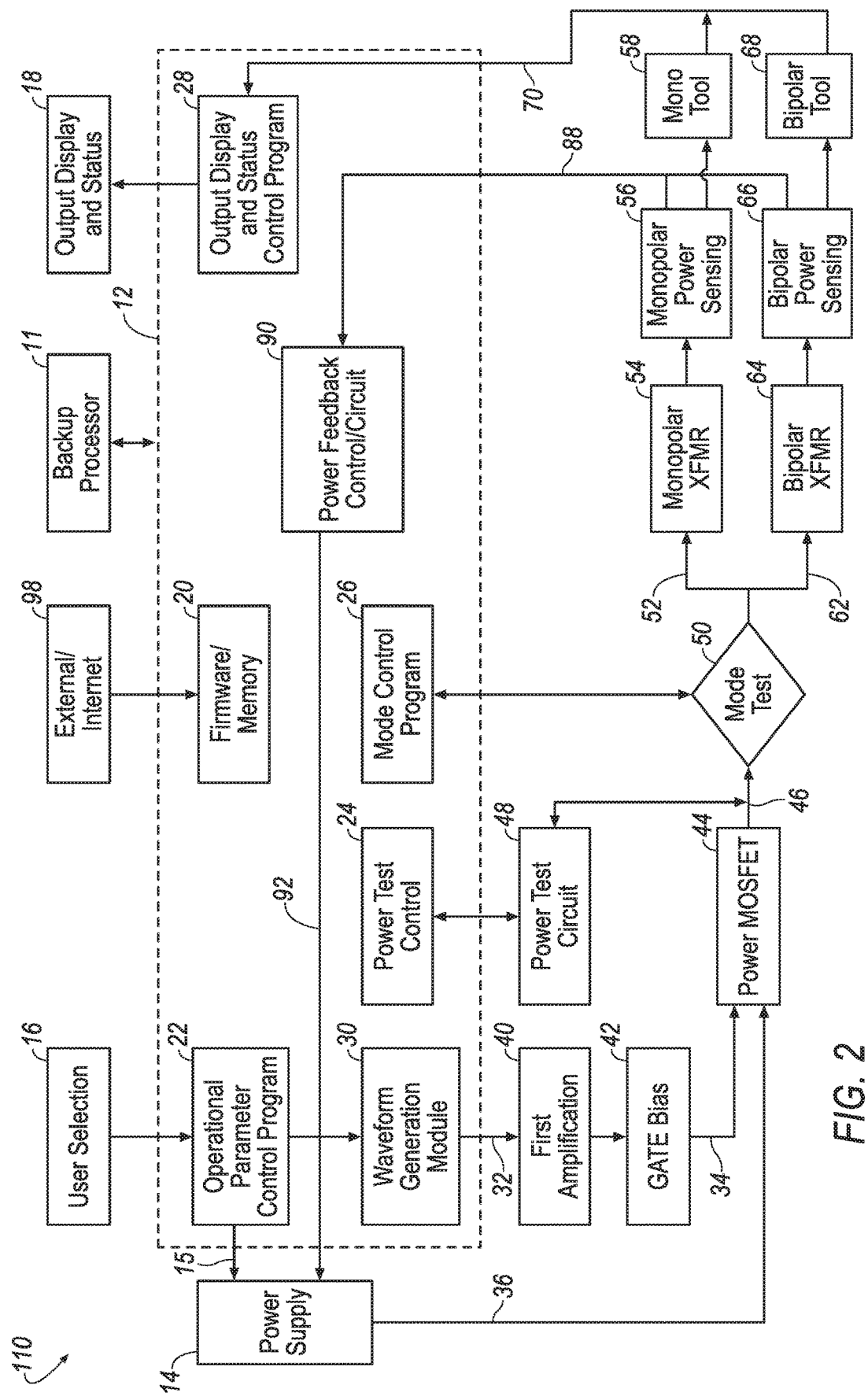
FIG. 2 illustrates a block diagram of a circuit for an electrosurgical instrument according to one aspect of the current invention.

In an alternate embodiment as shown in FIG. 2, power feedback control circuit 80 is incorporated in main processor 12 and connected to power sensing modules 56 and 66 by way of connector 88. Connector 88 may be a hardwired connector between electrosurgical handpiece to a console type unit which houses main processor 12 or connector 88 may be a wireless connection comprising receiver components also housed by a console unit. In this example, power control feedback circuit 80 comprises firmware and memory components 20 of main processor 12 which are programmed to provide algorithms for real time storage, testing, analysis and adjustment of power usage characteristic from power sensing modules 56 and 66. Power control feedback circuit 80 provides power adjustment signals directly to power supply 14 by way of connector 92 or by other connection means such as through connection 15 between operational parameter control program 22 of main processor 12 and power supply 14.

Based on a nominal voltage setting being supplied to power MOSFET via connector 36, one exemplary power supply 14 of the current invention has capability of voltage adjustment in an example set of ranges as described in Table 1 to maintain a constant power supply at the respective handpiece.

TABLE 1

| Nominal Voltage of Power Supply | Voltage Adjustment |
| --- | --- |
| 5 V | 1.5 to 7.5 V |
| 12 V | 4.5 to 15 V |
| 24 V | 9.0 to 30 V |
| 48 V | 18 to 58 V |

In addition to the exemplary settings of Table 1, a nominal voltage setting of −3.3 V or −5.0 V from the power supply 14 can be adjusted by +/−0.5V. The performance of the RF power output of an electrosurgical tool incorporating the RF circuit 10 of the current invention is enhanced by the power supply 14 being able to make precise voltage adjustments over a wide range of nominal voltage settings due to improved control functions provided by power feedback control circuit 80 based on real-time input from power sensing modules 56 and 66.

Output display and status control program 28 is incorporated in RF circuitry 10 utilizing programmable features of firmware and memory components 20 to provide output data to components of output display and status 18 which provide information to a user of an electrosurgical instrument utilizing RF circuitry 10. Components of output display and status control program 28 may include, but are not limited to, display screens, lights and alarms for providing status information of operational parameters such as power levels, temperatures, usage time, and operational mode selections as well as other operational information. Connector 70 figuratively illustrates a connection from monopolar handpiece or tool 58 and bipolar handpiece or tool 68 to output display and status control program 28, however, output display and status control program 28 may receive input from many other components and programs of main processor 12 to provide output status and alarms to a user. Other exemplary components include power test control 24, mode control program 26, and operations control program 22, as well as external input from power sensing modules 56 and 66, electrosurgical tool 58 and 68, and other sensors.

In an embodiment of the current invention, the characteristics of RF waveforms generated by waveform generation module 30 of RF circuitry 10 are determined by the surgical mode of operation selected by the user and input to main processor 12 via user selection 16. Enhanced RF waveform generation is provided by RF circuitry 10 of the current invention for a number of surgical modes of operation including CUT, CUT/COAG, HEMO, BIPOLAR HEMO, BIPOLAR TURBO, FULGURATE, ABLATE and others.

In one example of the current invention, RF circuitry 10 may be used to generate a continuous oscillating waveform signal such as a 4 MHz or 1.71 MHz frequency sine wave in the RF spectrum. A continuous waveform may be used to provide higher output power utilized for cutting tissue, but it may not provide optimal output power for hemostasis or stopping of bleeding. Waveform signals which are modulated with time-based on and off pulses or cycles at a particular duty cycle allow blood vessels to briefly cool and to shrink which stops the bleeding and promotes coagulation. In an embodiment of the current invention, wave generation module 30 of main processor 12 generates waveforms in a wide range of frequencies which can be modulated both by amplitude modulation and with a nearly unlimited range of on and off modulation cycles to customize the output power of to provide effective power level for hemostasis. Wave generation module 30 also provides multiple levels of discrete "packets" and "sub-packets" of waveform signal using pulse-modulation at different frequencies generated within a waveform for a single mode of operation of electrosurgical instrument.

In one embodiment an electrosurgical instrument using the RF circuitry 10 of the invention, a time-based modulation is used to produce a waveform with on and off pulses or duty cycle at certain low frequencies so as to generate an audible sound or hum in the electrosurgical instrument. This type of low-frequency modulation of waveforms at this audible range, termed "Soniquence," may provide an audible indicator to a user or surgeon as to which particular operational mode the electrosurgical instrument has been set. In another embodiment, the frequency of a signal output by waveform generator 30 of the current invention is adjustable and may range from 200 kHz to 4 MHz for a monopolar powered handpiece 58, and the output frequency may range from 200 kHz to 2.0 MHz for a bipolar powered handpiece 68.

Figure 3A:
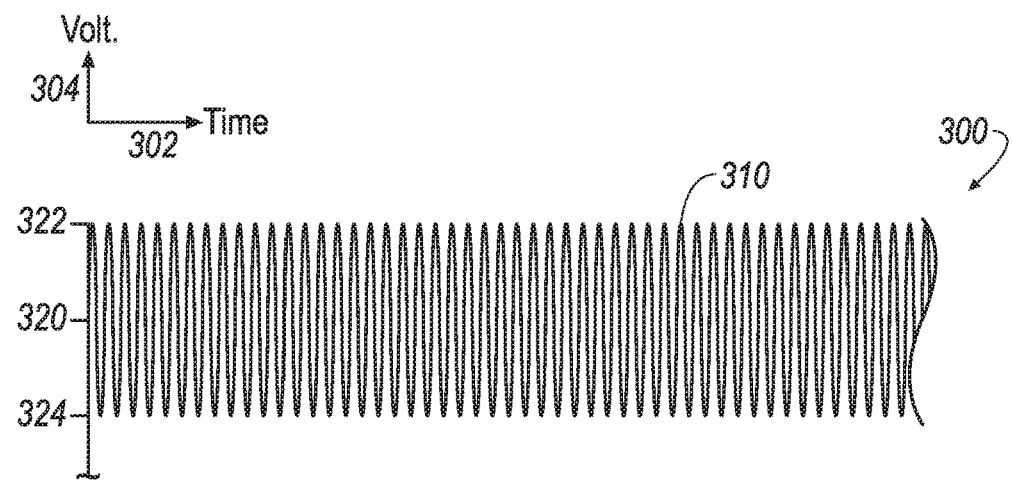
FIG. 3A illustrates a portion of an electrical waveform generated for a CUT mode of operation according to one aspect of the current invention.
Figure 3B:
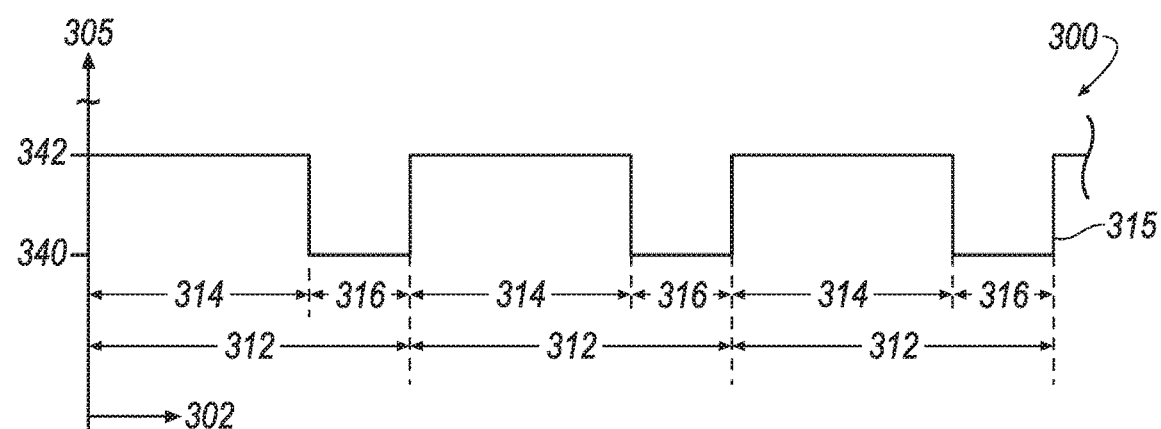
FIG. 3B illustrates a portion of a square duty cycle signal generated to provide a first level pulse-modulation signal according to one aspect of the current invention.
Figure 3C:
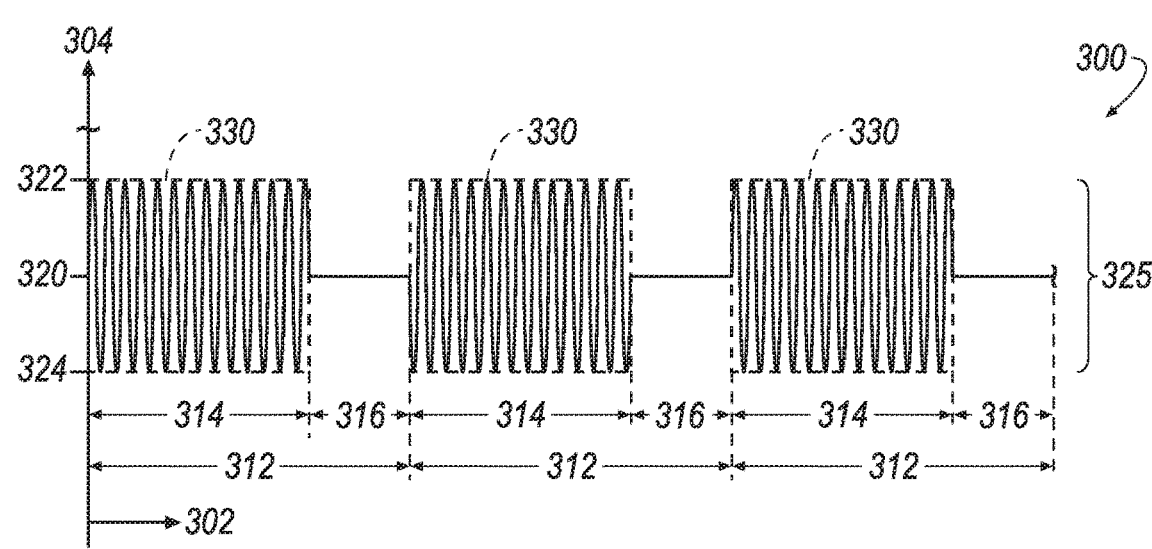
FIG. 3C illustrates a portion of the electrical waveform of FIG. 3A as modulated by the signal of FIG. 3B according to an example of the current invention.

FIG. 3A through 3C are time based graphs which are each related to the generation of a CUT waveform generated by waveform generator 30 for a CUT mode of operation 300. FIG. 3A illustrates an oscillating type base RF waveform 310 with a frequency in the RF spectrum. In one example, to execute the CUT procedure, a range of between 3.8 and 4 MHz has been shown to be effective in performing this procedure. FIG. 3B illustrates a square wave duty cycle or first pulse-modulation 315 wherein the waveform 310 is turned on and off to result in the waveform of FIG. 3C. FIG. 3C illustrates the resulting CUT waveform 325 of the current invention after the application of time-based pulse modulation as specified in FIG. 3B. In this example, CUT waveform 325 is generated by RF circuitry 10 and is used to provide RF power to a monopolar surgical handpiece for a CUT surgical procedure. In one embodiment of the current invention, CUT waveform 325 operates at a high average output power used for an exemplary electrosurgical procedure such as for cutting tissue.

Horizontal time axis 302 figuratively illustrates time for the waveforms and vertical voltage axis 304 figuratively illustrates voltage levels for each of the waveforms of FIG. 3A and FIG. 3C. In another embodiment, vertical axis 304 illustrates current or power level of a waveform. On/off axis 305 shows the on/off duty cycle as to when the waveform of FIG. 3A is applied to the surgical tool. Time axis 302, on/off axis 305, and voltage axis 304 are not intended to be interpreted literally to scale, but rather, provide a graphical representation of characteristics of each of the waveforms over time.

FIG. 3A illustrates base RF waveform 310 and, in this example, approximates a continuous 4 MHz sine wave fluctuating in a uniform manner about a nominal voltage 320 up to a high voltage 322 and down to a low voltage 324. Low voltage 324 can be either a low or zero positive voltage or, alternatively, it may be a negative voltage such as in the case of an alternating current. Voltage 320, 322 and 324 are shown as figurative levels.

In a first modulation of RF base waveform 310, waveform generation module 30 modulates base RF waveform 310 on and off according to the duty cycle of first pulse-modulation signal 315. First pulse-modulation signal 315 is ON when the level is high or set figuratively to level 342 and it is OFF when the level is low or set figuratively to level 340. The ON and OFF cycling is applied to base RF waveform 310 so that base RF waveform 310 is ON during the on-cycle 314 of first pulse-modulation signal 315 and base RF waveform 310 is OFF during the off-cycle 316 of first pulse modulation signal 315.

This pulsed interruption of base RF waveform 310 forms repeating discrete or pulsed "packets" of the base RF waveform 310. Packets 330 formed by first pulse-modulation signal 315 form a modulation envelope of a particular shape depending on the shape by the packet of underlying data of base RF waveform 310. A first modulation of RF base waveform 310 forms packets 330 each with a rectangular-shaped modulation envelope formed by the uniform fluctuation of base RF waveform 310 between figurative voltages 322 and 324 during the time first pulsed-modulation signal 315 is on. In another embodiment, a waveform packet may form a modulation envelope of another shape produced by a non-uniform, increasing or decreasing voltage or current levels during the time of an on-cycle. Alternate packet shapes may include but are not limited to triangular, saw tooth, square, star, stair step, or any other shape.

Packets 330 are repeated at a frequency and duty cycle matching that of first pulse-modulation signal 315 which, in this example, is particular to the CUT mode of operation. The CUT mode is ideal for segmenting and cutting tissue and the specific waveforms and frequencies described herein (although others may be used) have been found to be advantageous for this operation. More specifically, the duty cycle of ON/OFF switches rapidly between the sinusoidal ON state at max power to an off state, thereby enhancing cutting. The time to complete one ON and OFF cycle, or period 312, of first pulse-modulation signal 315 is 13.3 msec (millisecond), in one example, which approximates a 75 Hz frequency. The duration of on-cycle 314 of first pulse-modulation signal 315 is 12.7 msec and the duration of off-cycle 316 is 0.6 msec so that the signal operates at an approximate duty cycle of 96% with 96% ON AND 4% OFF. Likewise, CUT waveform 325 has a period 312 of 13.3 msec, an on-cycle 314 of 12.7 msec, an off cycle of 0.6 msec, approximates a frequency of 75 Hz and a duty cycle of 96%. The ON/OFF duty cycles provide a window of time from which feedback, measurements (including those described herein) may be obtained while no voltage is applied to the surgical area and, therefore, no interference from the surgical instrument inhibits measurements. In one example, such windows are achieved through a duty cycle of 90-98% with a frequency of 37 Hz to 75 Hz.

In an exemplary embodiment, CUT waveform 325 of RF circuitry 10 operates at a maximum average power of 120 watts and an average peak-to-power ratio of 100% to provide power to monopolar handpiece or monopolar tool 58 to perform an electrosurgical cutting procedure. While CUT waveform 325 provides a high power setting for the electrosurgical unit, it should be understood that other waveform frequency and duty cycle settings may be used and that other waveforms besides a sine wave or oscillating waveform may be used. Power settings including 200 watts may be achieved with the components described for RF circuitry 10 of the invention.

FIGS. 4A through 4H illustrate time based graphs which are each related to the generation of a CUT/COAG or BLEND waveform for a CUT/COAG mode or blend mode (CUT/COAG shall be treated as BLEND for purposes of the description) of operation 400. CUT/COAG mode of operation 400 employs multiple levels of waveform modulation. In the CUT/COAG mode, the surgeon desires to both cut tissue and coagulate to rapidly both cut and coagulate or cauterize the tissue area. As such, rapid OFF's during the normally ON state assist in providing very rapid intermittent cooling time during the ON state and also minimizes the depth of the penetration to prevent burning of the tissue area. A waveform design of an exemplary CUT/COAG mode of operation is also termed "Pulse Blend."

In one embodiment, CUT/COAG mode of operation 400 initially utilizes the same waveform as CUT waveform 325 of CUT mode 300 but is then further modulated with repeated on and off or pulsed modulation to generate waveforms which provide the rapid intermittent cooling time during the ON state. FIGS. 4B through 4D illustrate a second level of modulation and FIGS. 4E through 4H illustrate a third level of modulation in the generation of CUT/COAG waveform of the current invention 400.

Figure 4A:
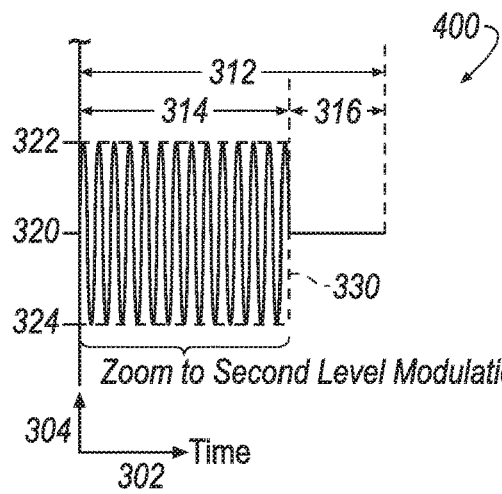
FIG. 4A illustrates a packet portion of the electrical waveform of FIG. 3C generated for a CUT/COAG mode of operation according to one aspect of the current invention.
Figure 4B:
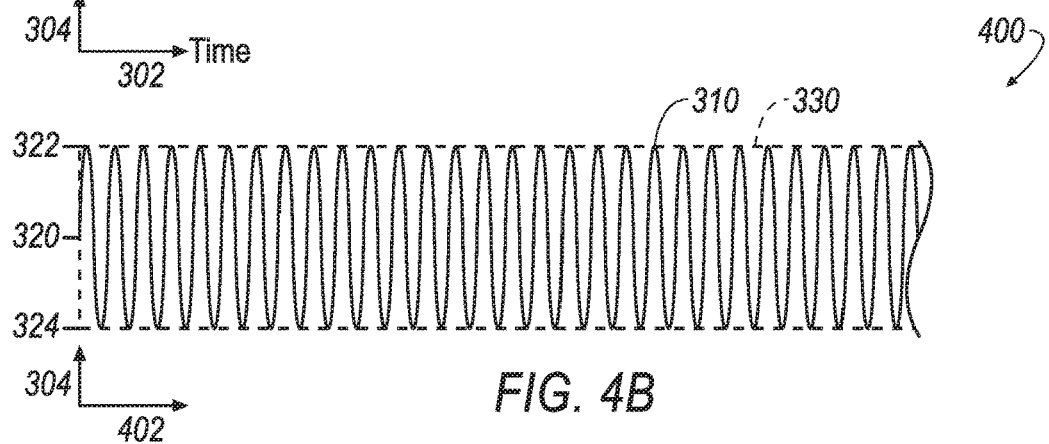
FIG. 4B illustrates an exploded view of a portion of the packet of the electrical waveform of FIG. 4A.
Figure 4C:
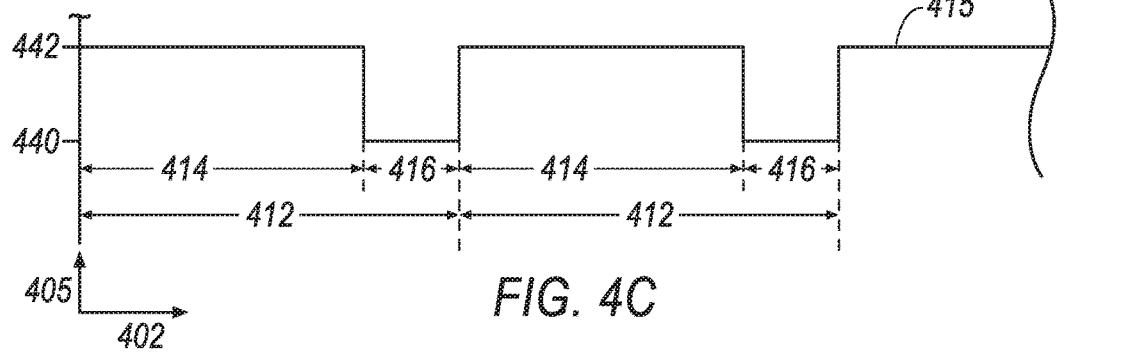
FIG. 4C illustrates a square duty cycle signal used to provide a second level pulse-modulation signal according to one aspect of the current invention.
Figure 4D:
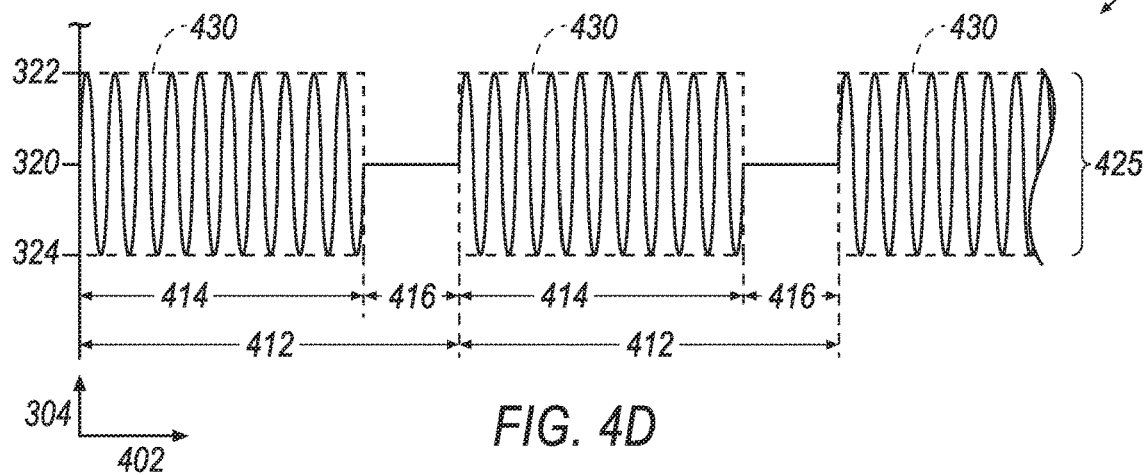
FIG. 4D illustrates a portion of the electrical waveform of FIG. 4B as modulated by the signal of FIG. 4C according to an example of the current invention.

FIG. 4A illustrates an exemplary packet 330 of RF base waveform 310 figuratively shown with time axis 302 as is also shown in FIG. 3C of the previously described CUT waveform 325. Likewise, CUT/COAG waveform 325 has a period 312 of 13.3 msec, an on-cycle 314 of 12.7 msec, an off cycle of 0.6 msec, approximates a frequency of 75 Hz and a duty cycle of 96%.

To illustrate a second level of modulation, a figurative "zoom" in of time which is applied to packet 330 so that FIG. 4B illustrates a smaller, "zoomed-in" portion of packet 330 against time axis 402. Time axis 402 represents a small portion of time within a packet 330. Waveform generation module 30 generates a second pulse-modulation signal 415 of FIG. 4C which is applied to base RF waveform 310 within packet 330 during an ON cycle 314. Second pulse-modulation 415 is illustrated as a square waveform with repeated, time-based duty cycle of ON/OFF states 405 forming pulses over time axis 402. Second pulse-modulation signal 415 is ON when the level is high (figuratively set to level 442) and it is OFF when the level is low (figuratively set to level 440). This additional on and off cycling is applied to packet 330 so that base RF waveform 310 is ON during an on-cycle 414 of second pulse-modulation signal 415 and OFF during an off-cycle 416 of second pulse-modulation signal 415. This pulsed interruption of base RF waveform 310 forms repeated sub-packets 430, each a discrete sub-packet of base RF waveform 310 within a packet 330. In this example, each sub-packet 430 also has a rectangular modulation envelope formed by the uniform fluctuation of base RF waveform 310 between figurative voltages 322 and 324.

Sub-packets 430 are repeated at a frequency and duty cycle matching that of second pulse-modulation signal 415 which, in this example, is particular to the CUT/COAG mode of operation 400. In this example, the time to complete one ON and OFF cycle, or period 412, of second pulse-modulation signal 415 is 0.093 msec approximating a 10.7 kHz frequency. The duration of on-cycle 414 of second pulse-modulation signal 415 is 0.069 msec and the duration of off-cycle 416 is 0.024 msec so that the signal 415 approximates a duty cycle of 74% with 74% ON and 26% OFF. Likewise, each sub-packet 430 of CUT/COAG waveform 425 has a period 412 of 0.093 msec, an on-cycle 414 of 0.069 msec, an off cycle of 0.024 msec, and approximates a frequency of 10.7 kHz and a duty cycle of 74%. One skilled in the art will recognize that other waveform frequencies, duty cycles, and modulation envelope characteristics may be used. For example, in another embodiment, period 412 is 0.069 msec approximating a 14.5 kHz frequency with a duty cycle of 74%. In one aspect, it has been found that a frequency range of 3 kHz to 19 kHz and a duty cycle of 1-90% provides some beneficial properties. Specifically, this frequency range, the penetration of the RF current is minimized to minimize burning. Also, the duty cycle provides sufficient spacing to permit cauterization. Lastly, this frequency creates an audible hum such that the surgeon can determine from listening as to what mode the surgical instrument is operating in. As the duty cycle moves from 1-90%, the resulting waveform moves more from hemo to cutting.

In FIG. 4D, sub-packets 430 are repeated and sequentially output at the 10.7 kHz frequency throughout the duration of the ON period 314 of packet 330. In one embodiment of the current invention, when an ON period 314 of packet 330 ends, the repetition of sub-packets 430 is halted at which time, off-cycle portion 316 is executed through the end of a single period 312 of waveform 325 and the process of repeating sub-packets 430 begins again with the beginning of the next occurrence of on-cycle 314 of a packet 330. The repetition of 10.7 kHz frequency of sub-packets 430 is timed to fit within the slower 75 Hz packets 330. For an exemplary packet 330 with a period of 12.7 msec, approximately 136.6 sub-packets 430 with a period of 0.093 msec will be generated by waveform generation module 30. Although base RF waveform 310 is OFF during off-cycles 316 as illustrated in this example, it should be understood further modulation can be applied and that waveform signals including RF waveform 310 may be generated during off-cycles 316 to provide a particular power level to an electrosurgical tool.

Figure 4E:
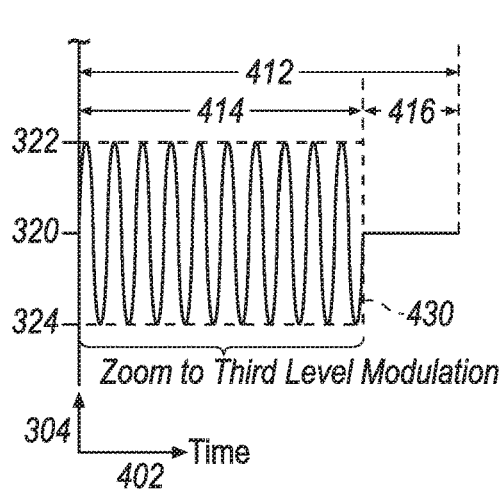
FIG. 4E illustrates a sub-packet portion the electrical waveform of FIG. 4D generated for a CUT/COAG mode of operation according to one aspect of the current invention.
Figure 4F:
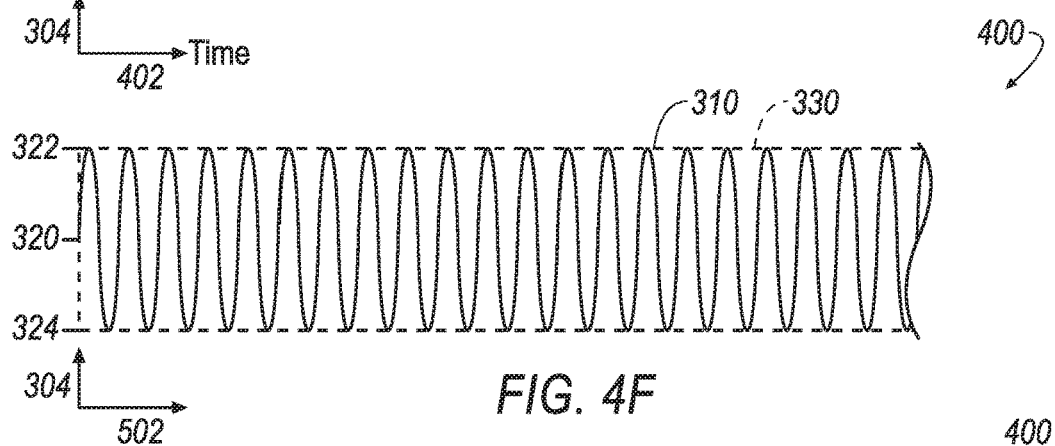
FIG. 4F illustrates an exploded view of a portion the sub-packet of the electrical waveform of FIG. 4E according to one aspect of the current invention.
Figure 4G:
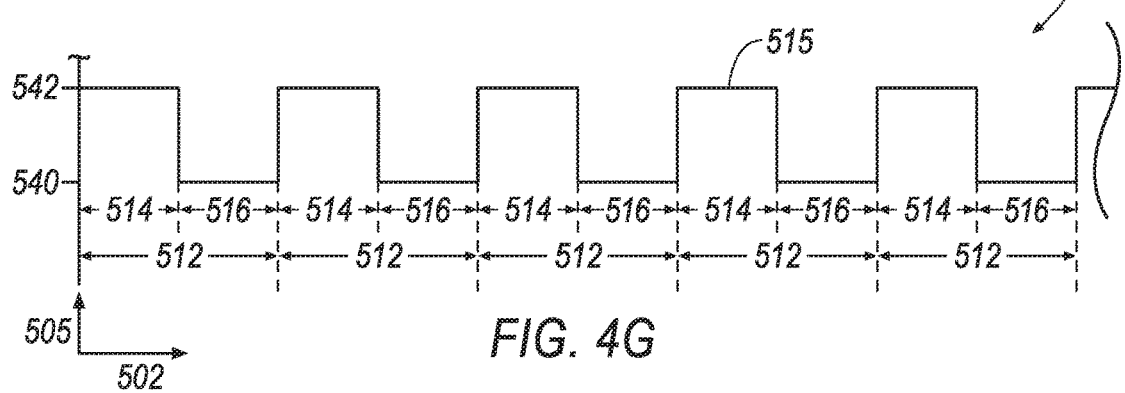
FIG. 4G illustrates a square electrical duty cycle signal used to provide a third level pulse-modulation signal according to one aspect of the current invention.

FIGS. 4E through 4H also show time based graphs related to the generation of a CUT/COAG waveform of CUT/COAG mode of operation 400. FIGS. 4E through 4H illustrate an example in which a third level modulation is applied to a waveform. For continuity, FIG. 4E illustrates an exemplary sub-packet 430 of waveform 425 with time axis 402 such as from FIG. 4D. To illustrate a third level of modulation, a figurative "zoom" in of time is applied to sub-packet 430 so that FIG. 4E illustrates a small, "zoomed-in" portion of sub-packet 430 with time axis 502. As such, time axis 502 represents a small portion of time within a sub-packet 430. Waveform generation module 30 generates a third pulse-modulation signal 515 of FIG. 4G which is applied to base RF waveform 310 within sub-packet 430 during an ON cycle 414. Third pulse-modulation 515 is illustrated as a square waveform with repeated, time-based duty cycle of ON/OFF states 505. Third pulse-modulation signal 515 is ON when the level is high (figuratively level 542) and it is OFF when the signal level is low (figuratively level 540). This on and off cycling is applied to sub-packet 430 so that base RF waveform 310 is turned on during the on-cycle 514 of third pulse-modulation signal 515 and base RF waveform 310 is turned off during the off-cycle. This pulsed interruption of base RF waveform 310 forms yet another level of repeated sub-packets 530 termed "second level sub-packets 530" or "sub-sub packets 530" within sub-packet 430. In this example, each "sub-sub packet 530" also has a rectangular shape formed by the uniform fluctuation of base RF waveform 310 between figurative voltages 322 and 324. Multiple levels of modulation may be applied and multiple "N" levels of sub-packets or "sub N packets" of waveform may be programmed to provide finely tuned power levels which may be applied to an electrosurgical handpiece.

Second level sub-packets 530 are repeated at a frequency and duty cycle matching that of third pulsed-modulation signal 515 and are particular to CUT/COAG mode of operation 400. The time to complete one ON and OFF cycle, or period 512, of third pulse-modulation signal 515 is 0.0005 msec approximating a 2 MHz frequency. The duration of on-cycle 514 of third pulse-modulation signal 515 is 0.00025 msec and the duration of off-cycle 516 is 0.00025 msec so that this signal approximates a duty cycle of 50% with 50% ON and 50% OFF. Likewise, second level sub-packets 530 as shown in CUT/COAG waveform 525 each have a period 512 of 0.0005 msec, an on-cycle 514 of 0.00025 msec, an off cycle 516 of 0.00025 msec, and approximates a frequency of 2 MHz and a duty cycle of 50%. One skilled in the art will recognize that other waveform characteristics may be used.

Figure 4H:
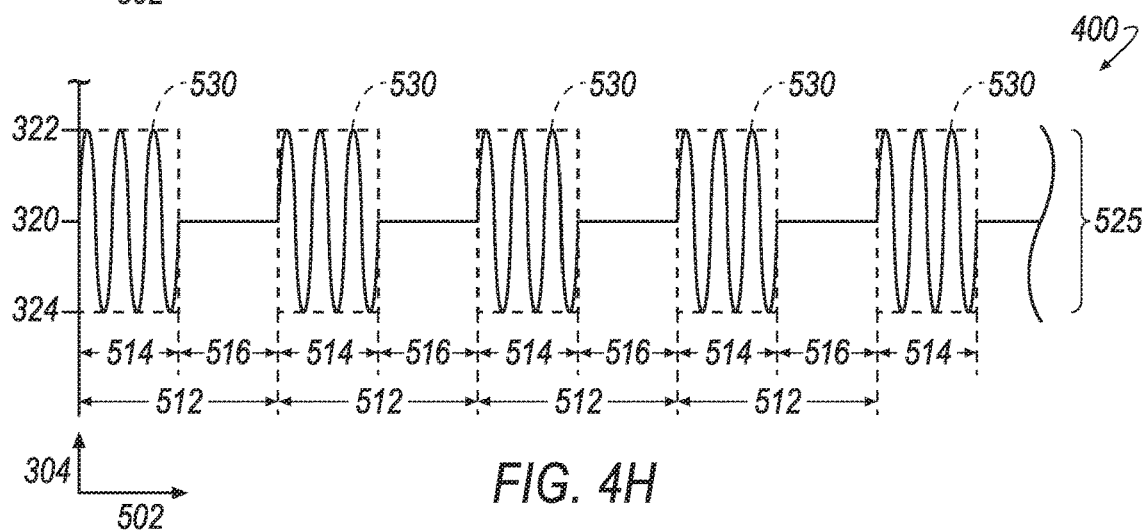
FIG. 4H illustrates a second-level sub-packet portion of the electrical waveform of FIG. 4F as modulated by the signal of FIG. 4G according to an example of the current invention.

In FIG. 4H, second-level sub-packets 530 are repeated and sequentially output at approximately a 2 MHz frequency throughout the duration of the ON period 414 of sub-packet 430. In this example, when the ON period 414 of sub-packet 430 of FIG. 4E ends, the repetition of second-level sub-packets 530 is halted at which time, sub-packet off-cycle portion 416 is executed through the end of a single period 412 of waveform 425. The process of repeating second-level sub-packets 530 begins again with the beginning of the next occurrence of sub-packet 430. The repetition of the 2 MHz frequency second-level sub-packets 530 is timed to fit within both the slower 10.7 kHz sub-packets 430 and still slower 75 Hz packets 310. For an exemplary sub-packet 430 with a period of 0.093 msec, approximately 372 second-level sub-packets 530 with a period of 0.00025 msec will be generated by waveform generation module 30. Although base RF waveform 310 is OFF during off-cycles 316, 416 and 516 in this example, it should be understood that waveform signals may be utilized during these off-cycles to provide a particular power level to an electrosurgical tool.

In this example, CUT/COAG waveform for CUT/COAG mode of operation 400 is generated by RF circuitry 10 and is used to provide RF power to a monopolar surgical handpiece for a CUT/COAG surgical procedure combining cutting and hemostasis of tissues in one surgical procedure. In an embodiment, CUT/COAG mode 400 operates at a maximum power setting of 84 watts and an average peak-to-power ratio of 70% as may be desired for an electrosurgical procedure providing both cutting and coagulation capabilities. It should be understood that other waveforms may be used to provide a waveform signal desirable for a surgical CUT/COAG procedure.

In another embodiment of the current invention, waveform generation module 30 provides waveforms for a HEMO mode of operation. In one embodiment, HEMO mode of operation employs multiple levels of waveform modulation. In the HEMO mode, the surgeon desires to primarily and rapidly coagulate or cauterize the tissue area utilizing a combination of pulsed signal packets for coagulation termed "Pulse Coag." In one example, HEMO mode of operation employs two levels of modulation with different waveform duty cycles frequencies.

An exemplary HEMO mode of operation employs base RF waveform 310 with an oscillating waveform and a frequency of 4 MHz, a first level of modulation with a 96% duty cycle, and a second level of modulation with a 50% duty cycle and with the following exemplary conditions:

Hemo:

| First modulation packet period 312 | 13.3 msec |
| First modulation packet on-cycle 314 | 12.7 msec |
| First modulation packet off-cycle 316 | 0.6 msec |
| Second modulation sub-packet period 412 | 0.093 msec |
| Second modulation sub-packet on-cycle 414 | 0.0465 msec |
| Second modulation sub-packet off-cycle 416 | 0.0465 msec |

In an exemplary embodiment, HEMO waveform operates at a maximum average power of 60 watts and an average peak-to-power ratio of 35% to provide power to monopolar handpiece or monopolar tool 58.

In another embodiment of the current invention, RF circuitry 10 is utilized to provide power to bipolar handpiece 68. In one such example, waveform generation module 30 provides waveform signals for a BIPOLAR HEMO mode of operation utilizing a base RF waveform frequency lower than that used for monopolar power, but still utilizing one or more levels of waveform modulation. An exemplary BIPOLAR HEMO mode of operation employs a base RF waveform 310 with an oscillating waveform with a frequency of 1.7 MHz and utilizes one level of modulation with a duty cycle approximates a 48% to 50% duty cycle and approximates a 37.5 Hz frequency using the following conditions:

Bipolar Hemo:

| First modulation packet period 312 | 26.6 msec |
| First modulation packet on-cycle 314 | 12.7 msec |
| First modulation packet off-cycle 316 | 13.9 msec |

In an exemplary embodiment, BIPOLAR HEMO waveform operates at a maximum average power of 40 watts and an average peak-to-power ratio of 35% to provide power to bipolar handpiece 68 or other bipolar tool.

In another embodiment of the current invention, waveform generation module 30 of RF circuitry 10 is utilized to provide waveforms for a BIPOLAR TURBO mode of operation. An exemplary BIPOLAR TURBO mode of operation employs base RF waveform 310 with an oscillating waveform with a frequency of 1.7 MHz and utilizes one level of modulation with a 96% duty cycle using the following conditions:

Bipolar Turbo:

| First modulation packet period 312 | 13.3 msec |
| First modulation packet on-cycle 314 | 12.7 msec |
| First modulation packet off-cycle 316 | 0.6 msec |

In an exemplary embodiment, BIPOLAR TURBO waveform operates at a maximum average power of 120 watts to provide power to bipolar handpiece or bipolar tool 68. Another example of a waveform of the current invention supplies a maximum average power of 90 watts for a bipolar surgical mode of operation.

FIG. 5A through 5E are time based graphs which are each related to the generation of a triangular waveform for a mode of operation 700. Vertical axis 704 figuratively illustrates a voltage level and horizontal time axis 702 figuratively illustrates time for the waveforms of FIGS. 5A, 5C, and 5E. In another embodiment, vertical axis 704 illustrates current or power level of a waveform. Time axis 702 and voltage axis 704 are not intended to be interpreted literally to scale, but rather, provide a graphical representation of characteristics of each of the waveforms of FIGS. 5A, 5C and 5E.

Figure 5A:
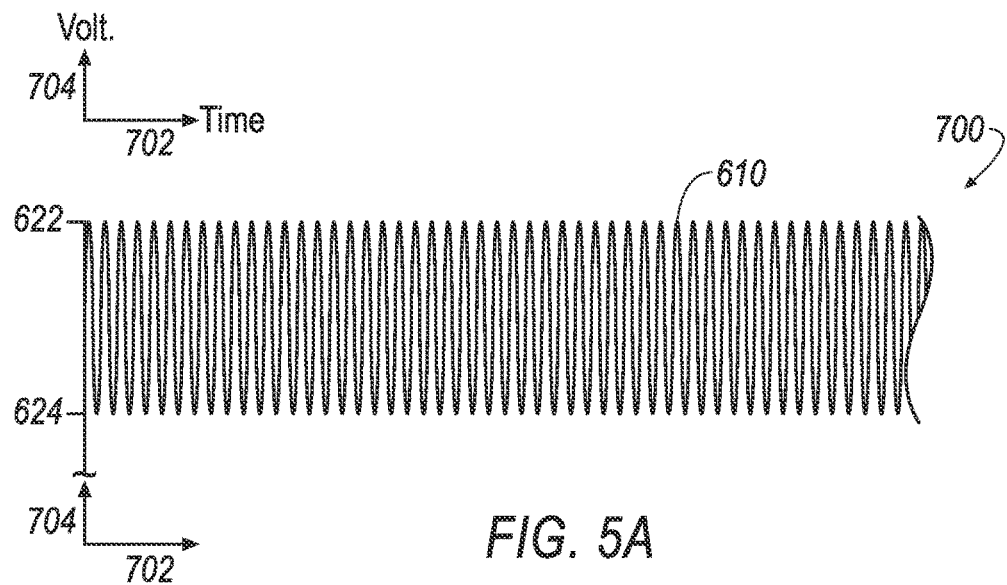
FIG. 5A illustrates a portion of an electrical waveform according to an example of the current invention.
Figure 5B:
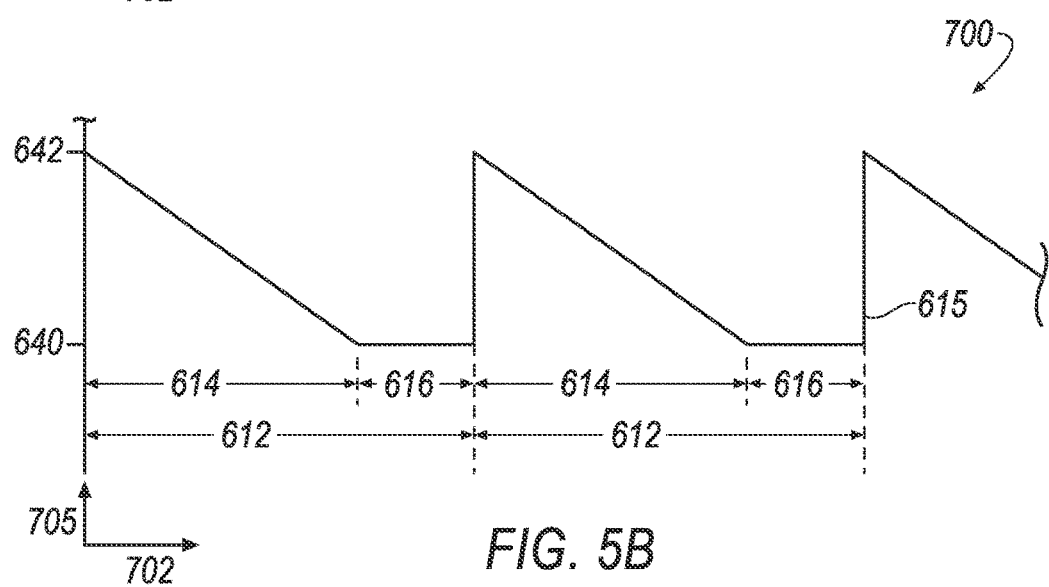
FIG. 5B illustrates a portion of a triangular electrical signal used to provide a first modulation signal according to an aspect of the current invention.
Figure 5C:
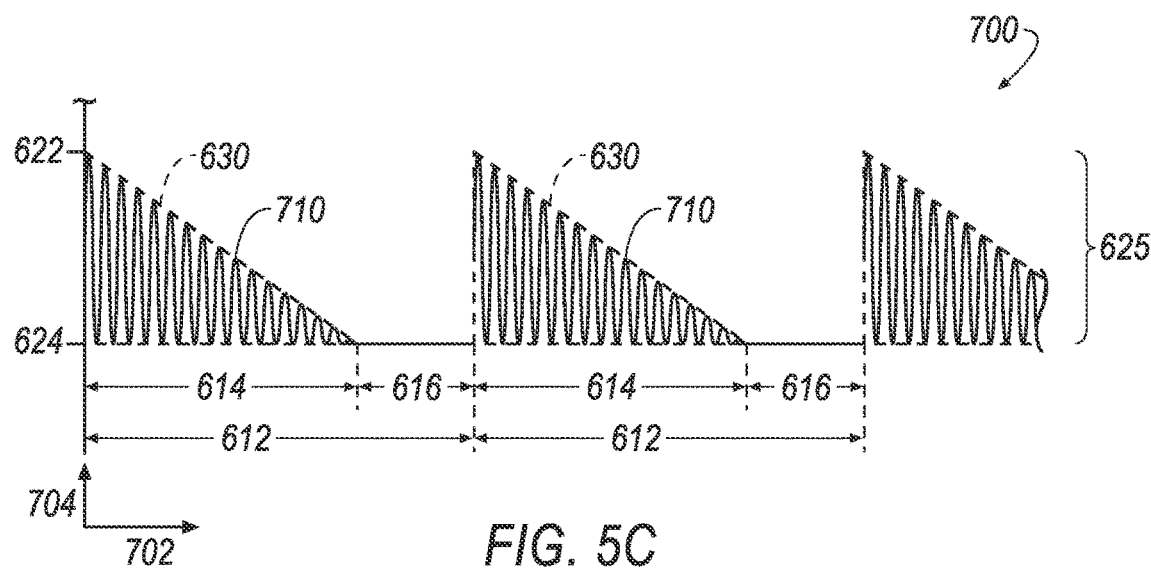
FIG. 5C illustrates a portion of the electrical waveform of FIG. 5A as modulated by the modulation signal of FIG. 5B according to an aspect of the current invention.

FIG. 5A illustrates an oscillating waveform, base RF waveform 610, with a frequency in the RF spectrum. FIG. 5B illustrates a triangular modulation signal 615 which is formed of a time-based, repeating signal of changing amplitude 705 or level over time. Triangular modulation signal 615 figuratively illustrates a modulation effect over time axis 702 and amplitude axis 705 which is used to modulate base RF waveform 610 to provide triangular waveform 625 of FIG. 5C. Triangular modulation signal 615 has a repeating triangular form of decreasing amplitude from upper level 642 to lower level 640 and is applied to base RF waveform 610 in such a fashion as to modulate base RF waveform 610 to form a repeated signal of decreasing voltage 704 over time 702. This first modulation of RF base waveform 610 forms packets 630 each with a triangular-shaped modulation envelope 630 formed by the decreasing amplitude or voltage of waveform 710 from a figurative maximum level of 622 down to a figurative minimum level of 624. Low voltage 624 can be either a low or zero positive voltage or, alternatively, it may be a negative voltage such as in the case of an alternating current. Triangular waveform 625 illustrates a waveform with triangular shaped packets 630 or modulation envelopes which repeat at an interval or period 612. In this example, triangular waveform 625 is ON during on-cycle portion 614 and OFF during off-cycle portion 616. In this example, off-cycle equals is set to voltage level 624 which may be a zero voltage value or be set to any other voltage level as desired for providing a particular output power level to an electrosurgical tool.

Figure 5D:
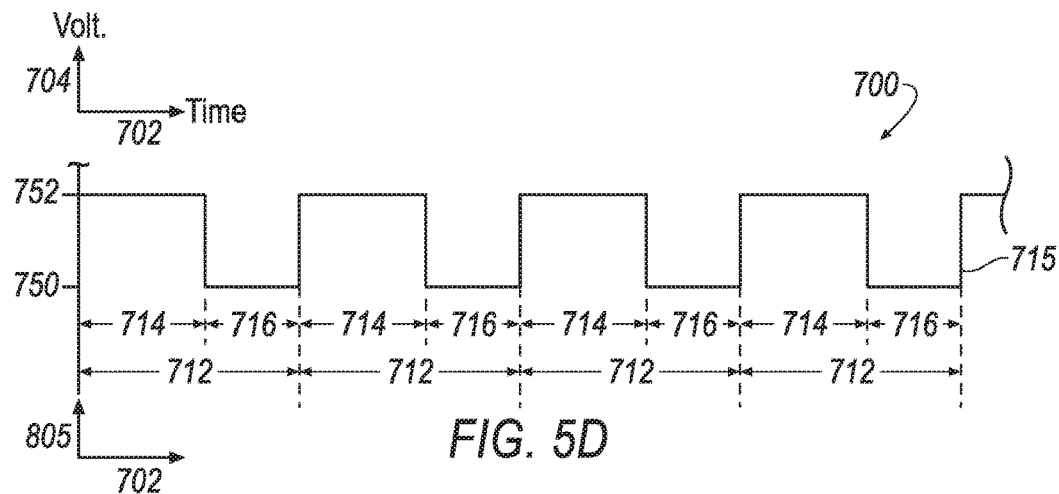
FIG. 5D a illustrates a square duty cycle signal used to provide a second level pulse-modulation signal according to one aspect of the current invention.
Figure 5E:
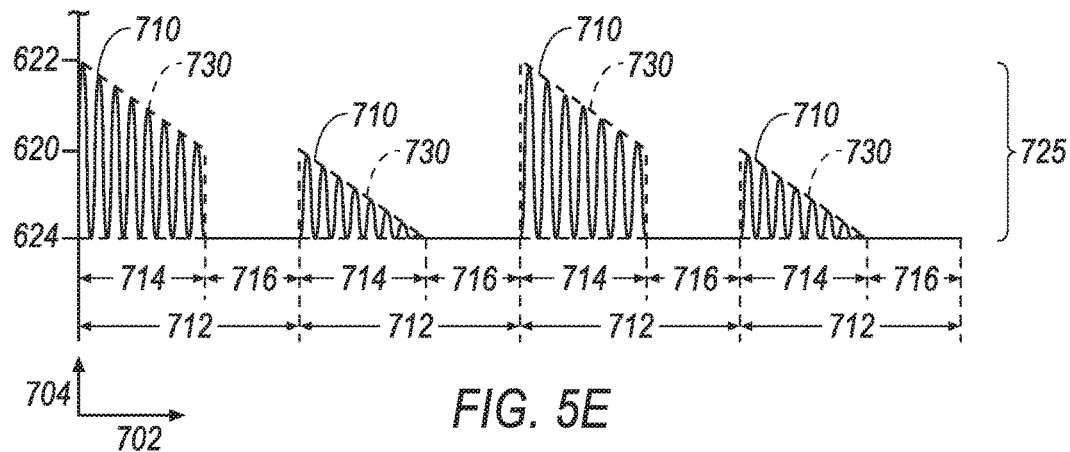
FIG. 5E illustrates a portion of the electrical waveform of FIG. 5C as modulated by the signal of FIG. 5D according to an example of the current invention.

In a second level of modulation of triangular waveform 625, FIG. 5D illustrates a square wave duty cycle 715 which is used to modulate triangular waveform 625. Square wave duty cycle 715 is ON when the signal level of on/off axis 805 is high (figuratively level 752) and it is OFF when the signal level is low (figuratively level 750). This on and off cycling is applied to triangular waveform 625 so that waveform 710 is turned on during the on-cycle 714 of square modulation signal 715 and off during the off-cycle 716. This pulsed interruption of triangular waveform 625 forms discrete, repeated sub-packets 730. FIG. 5E illustrates a waveform 725 of the current invention after a second modulation of triangular waveform 625 by the time-based pulses of square modulation signal 715. Each sub-packet 730 has a non-uniform shape formed by the pulsed interruption of triangular-shaped packets 630. In this example, a non-uniform sub-packet 730 with period 712, on-cycle 714 and off cycle 716 is generated by RF circuitry 10 and is used to provide RF power to a surgical handpiece for an exemplary surgical procedure. As such, waveform generation module 30 may be used to generate waveforms in a wide range of characteristics including a nearly unlimited number of packet shapes, modulation envelope shapes, pulse frequencies and levels of modulation.

Figure 6:
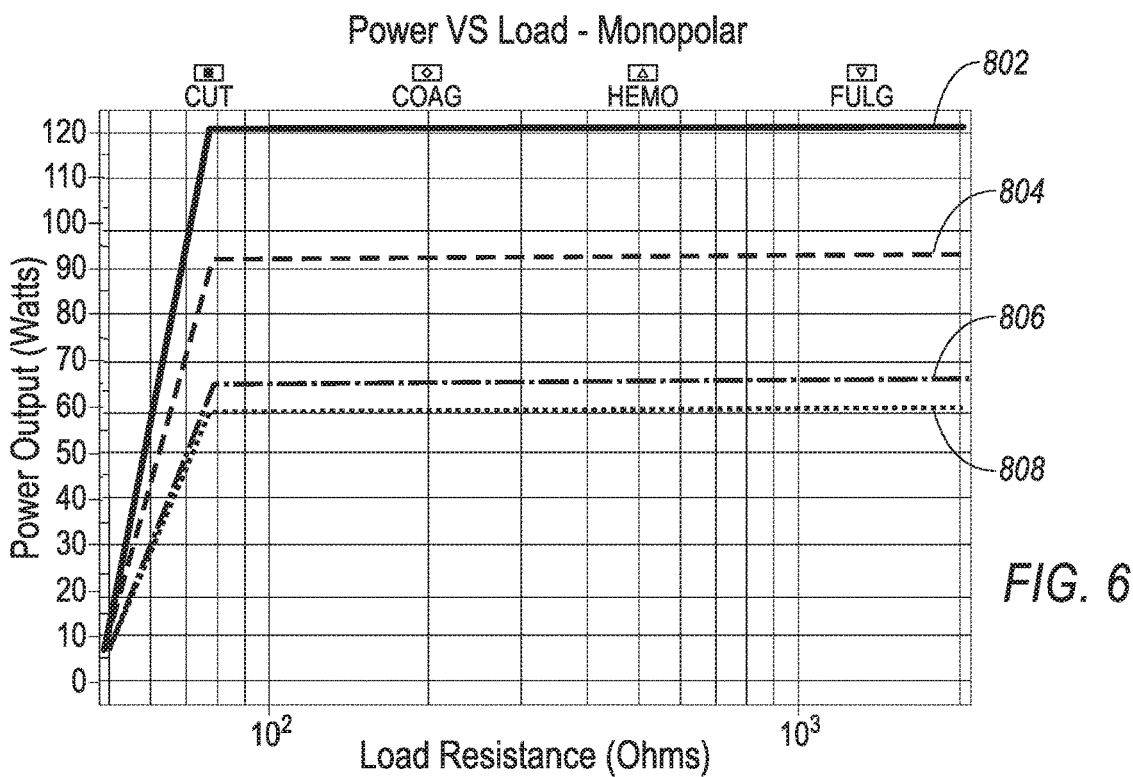
FIG. 6 illustrates a graph of load resistance versus output power level according to an aspect of the current invention.

FIG. 6 graphically illustrates the stabilizing effect of a real-time feedback system of power sensing circuits 56 and 66 providing data to power feedback control circuit 80 for adjustment of power supply 14. X-axis of FIG. 6 represents load resistance as measured in ohms on a Log 10 base scale from 0 to approximately 2000 ohms. In one example, load resistance is measured directly at power sensing circuits 56 and 66. In another example, load resistance is calculated using data collected by power sensing circuits 56 and 66 and then combined with logic or algorithm programs of power feedback control circuit 80. Y-axis of FIG. 6 represents the power output (in watts) by RF circuitry 10 and as produced, for example, at output signal 46 from power MOSFET 44. It should be understood that other measurement points may be used to monitor and characterize the output power of the current invention with respect to load resistance. Each of the plotted lines of data on the graph of FIG. 6 represents specific mode of surgical operation of an electrosurgical tool of the current invention. For example graph line 802 represents the power load versus power output for an exemplary CUT mode of operation 300 as discussed with FIGS. 3A through 3C. Graph line 804 represents the power load versus power output for an exemplary CUT/COAG mode of operation 400 as discussed with FIGS. 4A through 4H. Graph line 806 represents an exemplary HEMO mode and graph line 808 represents an exemplary FULGURATE mode of electrosurgical operation. The graph of FIG. 6 illustrates a generally constant power output which produced over varying load resistance values. Each of these graph lines, while operating at different output power level (watts) on the y-axis, are stable, if not flat over the varying Load Resistance (ohms) of x-axis illustrating the stabilizing, targeting impact of the real-time adjustments to power supply 14 as provided by power feedback circuit 80 of the current invention.

In an example of operation of RF circuitry 10 of the current invention, a surgeon or user may provide user selection 16 as input for a number of operating parameters which are used to operate the surgical instrument. The operating parameters may include, but are not limited to, a surgical mode of operation, a power setting, and a power mode. In one example, the operating parameters are communicated to the electrosurgical instrument by an input to user selection 16 such as activating a finger switch on a handpiece, activating a foot switch, or by touching a touchscreen feature or a button on an input screen. User selection 16 is communicated to operations control program 22 of main processor 12 to and is used to execute stored control programs for the generation of waveform signals by waveform generation module 30. In one example, user selection 16 inputs a CUT surgical mode of operation with a monopolar handpiece at a desired power setting and waveform generation module 30 generates CUT waveform 435 as described with FIGS. 3A through 3C. In another example of operation in which where user selection 16 has selected a CUT/COAG surgical mode of operation utilizing a monopolar handpiece, waveform generation module 30 generates CUT/COAG waveform 400 as described with FIGS. 4A through 4H. It should be understood that any number programs may be stored and executed to produce any number of waveform signals based on user selection 16.

Based on input of user selection 16, waveform generation module 30 outputs the selected waveform signal 32 for amplification 40 and inputs a gate bias 42 signal to power amplification MOSFET 44. Concurrently, operations control program 22 detects the selected power level and communicates with power supply 14 to provide appropriate power supply 14 level to power MOSFET 44 to amplify output waveform signal 34. Output RF power 46 from power amplifier MOSFET 44 is tested at mode test 50 to verify that the correct handpiece, either monopolar or bipolar, will be activated based on user selection 16 input to mode control program 26. Mode test 50 verifies that output RF power 46 matches the expected values of mode control program 26 parameters. Depending on mode of power selected and verified, power signal 52 or 62 is then fed to either monopolar transformer 54 or bipolar transformer 64. In each case, transformer 54 or 64 delivers power to the associated electrosurgical handpiece 58 or 68 or surgical tool for use in performing the selected surgical procedure such as CUT, CUT/COAG, Pulse Blend or other selected mode of operation. In another example of the invention, additional input from user selection 16 may be required, such as an input signal from button activation or from a foot switch, before the activation of power signal 52 or 62 to handpiece 58 or 68.

While in operation, exemplary monopolar sensing circuits 56 or bipolar sensing circuits 66 collect measurement data related to power level and load resistance of the electrosurgical handpiece during a surgical procedure. The collected readings are fed to power feedback control circuit 80 for analysis and comparison with target power levels. Power adjustment control signals are sent from feedback control circuit 80 to power supply 14 when needed. Parametric measurement data from power sensing circuit 56 or 66 is continuously sent to power feedback control circuit 80 for determination of any power adjustment which is then fed to power supply 14 to provide output power level that continuously matches the desired power level at the electrosurgical handpiece.

In one embodiment, output display and status components 18 receive data from output display and status control program 28 and power sensing circuits 56 or 66 in order to provide real-time status of operational conditions and alarms so that current information is provided to the surgeon or user of the electrosurgical instrument.

Figure 7:
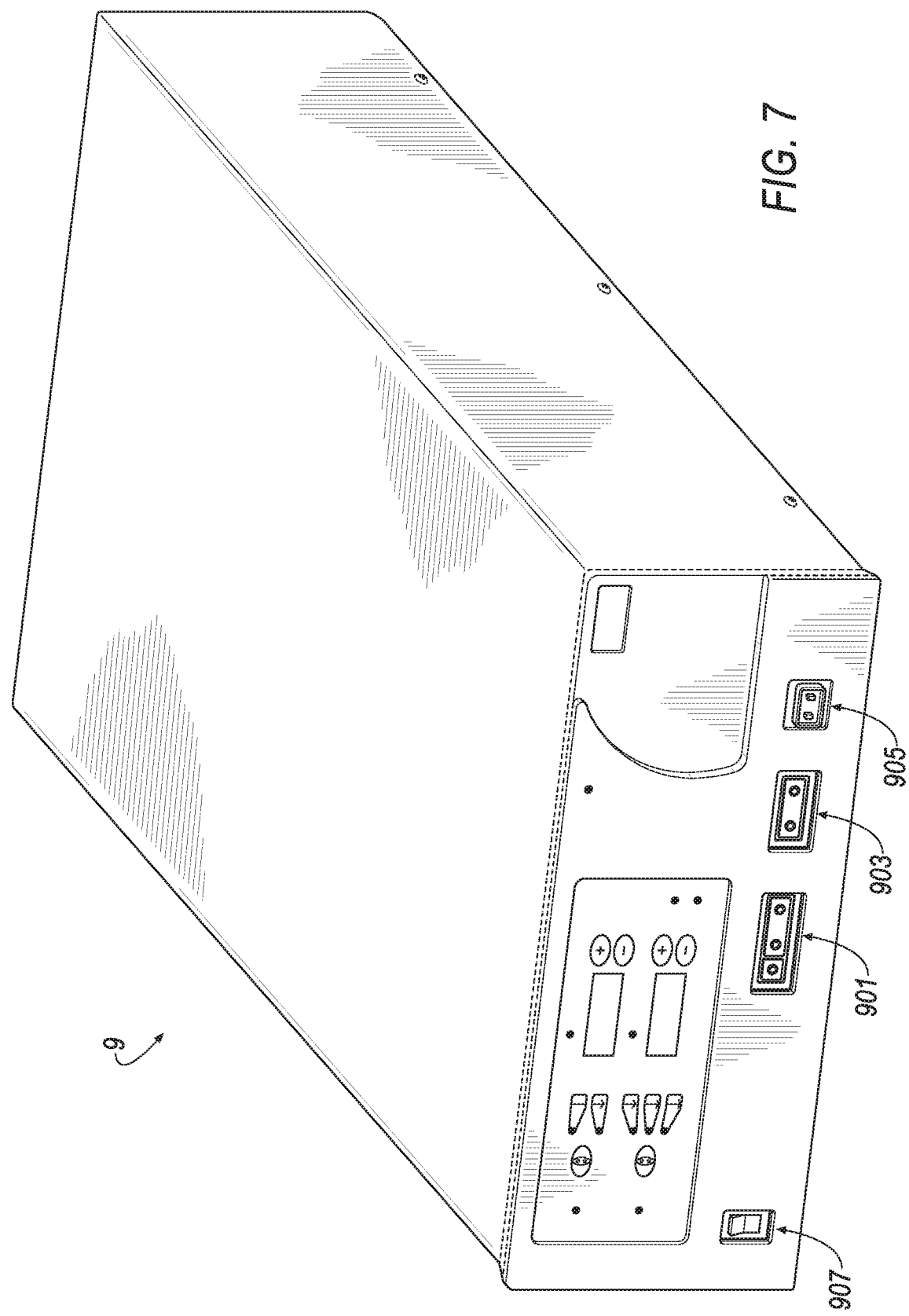
FIG. 7 illustrates a perspective view of an RF Generator for an Electrosurgical Instrument according to an aspect of the current invention.

Referring now to FIG. 7, one aspect of an RF generator for an electrosurgical instrument 9 is shown and described. The RF generator 9 encapsulates circuitry 10 therein that is described with reference to the previous figures. The RF generator 9 is shown, in one embodiment, as generally a rectangular container that has top, sides, rear and a bottom portion that contains the circuitry 10. Additionally, the RF generator 9 has a front face that contains various switches, displays, controls and plugs. For instance, the front face of RF generator 9 includes a monopolar plug 901 for connecting a monopolar electrosurgical instrument, a bipolar plug 903 for connecting a bipolar electrosurgical instrument, and a neutral or ground 905.

Figure 8:
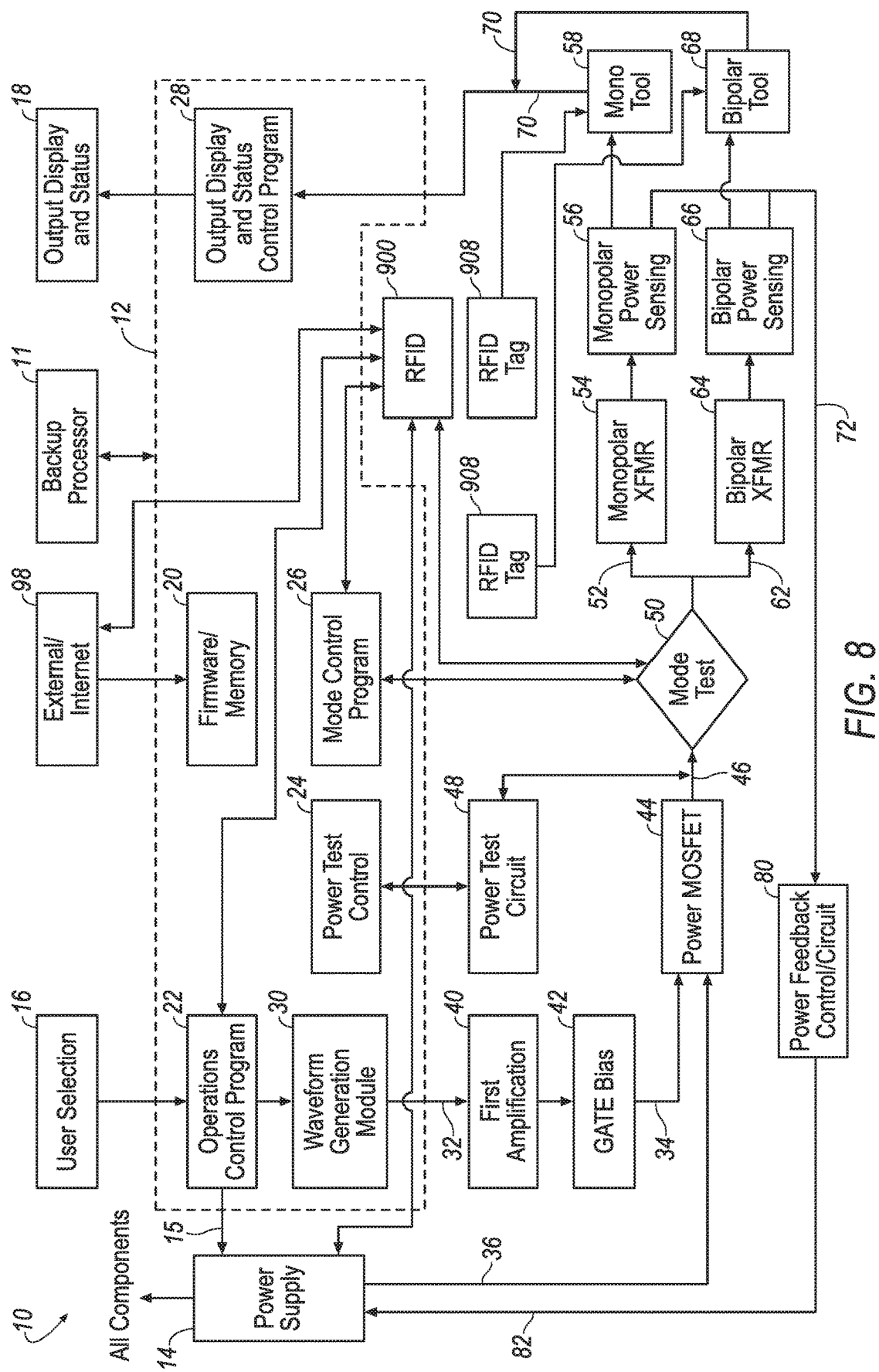
FIG. 8 illustrates a block diagram for an RF Generator for an Electrosurgical Instrument according to an aspect of the current invention.

Referring now to FIG. 8, circuitry 10 is shown having radiofrequency identification or RFID reader and writer 900. RFID reader and writer 900 reads and writes tag information to a RFID tag. As such, RFID reader and writer 900 is in radiofrequency communication with an RFID tag on monopolar handpiece 58 and bipolar handpiece 68 as will be described in greater detail. RFID reader and writer 900 reads information from monopolar handpiece 58 or bipolar handpiece 68 and provides that information to external internet 98, mode control program 26, operations control program 22, power supply 14, and mode test 50. Likewise, information is passed from any one of the aforementioned components, particularly external internet 98, to monopolar handpiece 58 or bipolar handpiece 68.

Referring now to FIG. 9, an electrosurgical handpiece is shown connected to a plug 911 through a cable 904. The cable provides electrosurgical current to the electrosurgical handpiece. The electrosurgical handpiece is used for electrosurgical operations and may be either a monopolar or bipolar type. As shown in FIG. 10, the plug 911 includes a plug body 902 that has electrodes 906 extending therefrom for electrically mating with monopolar plug 901 or bipolar plug 903. It will be understood that the electrosurgical handpiece shown in FIGS. 9 and 10 are bipolar electrosurgical instruments and therefore mate with bipolar plug 903.

Figure 11:
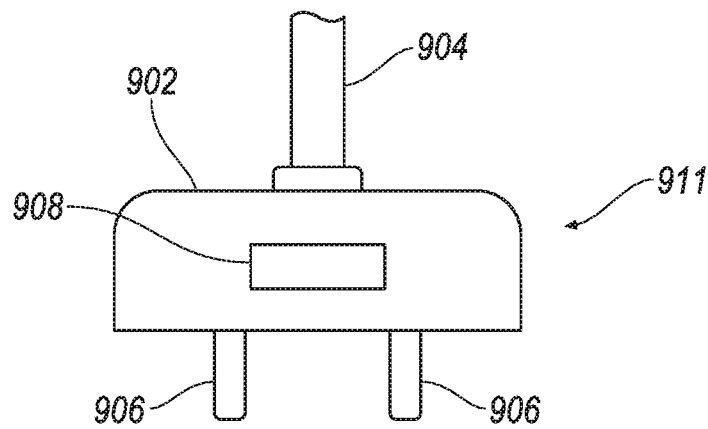
FIG. 11 illustrates a plan view of a RFID plug used in connection with an RF Generator for an Electrosurgical Instrument according to an aspect of the current invention.

Referring to FIG. 11, plug 911 is shown having an RFID tag 908. RFID tag 908 is an RFID tag that can be active, passive, or battery assisted passive. RFID tag 908 can, in one embodiment, has encoded thereon information about the electrosurgical instrument to which the plug 911 is connected. For example, RFID tag 908 may include information such as whether the electrosurgical instrument is monopolar or bipolar. By this way, the information from RFID tag 908 can be used by the processing of RF generator 9 to only provide power to the electrosurgical instrument if the electrosurgical instrument is plugged into the correct plug. For example, if the electrosurgical instrument is a bipolar instrument, then power would only be provided to the electrosurgical instrument if the plug is plugged into bipolar plug 903. Further, the information encoded on the RFID tag 908 may include the type of surgical procedure that will be performed with the electrosurgical instrument, such as spinal, OB/GYN or other surgical procedures. For example, the RFID tag may be encoded once the electrosurgical instrument is sold to a surgeon and for that surgeon. Thus, when the RF Generator 9 is provided the information from RFID tag 908, the predetermined settings of the RF Generator 9 can be set for that particular surgeon or the surgical procedures for which the surgeon is trained or performs. In this situation, RF generator 9 would thereby provide specific settings conducive to the specific surgical procedure in response to reading the information from RFID tag 908.

Further, the information contained in the RFID tag 908 may include the name or skill level of the surgeon who is performing the surgical procedure. In this way, the information from RFID tag 908 may be communicated back to RF generator 9 to set specific conditions desired by that particular surgeon. RFID tag 908 may further include geographical information such that the electrosurgical instrument is only permitted to be used in certain geographic locations. For example, if the electrosurgical instrument is not permitted to be used in a particular country, RFID tag 908 may be encoded with permitted countries, where such countries are matched to a lookup table or other storage of permitted locations in the RF generator 9 as well as GPS information provided by the RF generator 9 that provides a location of the RF generator 9, whereby power is only provided to the electrosurgical instrument if the GPS information indicates that the RF generator 9 is located in a permitted country.

Licensing information may also be recorded on RFID tag 908. For example, an electrosurgical instrument may only be licensed for use with a specific RF generator 9. In this case, IDs or identifiers in RFID tag 908 may be matched to those in a lookup table on RF generator 9 to ensure that the electrosurgical instrument is properly licensed for that particular RF generator.

The information encoded on RFID tag 908 may further be updated by RF generator 9. Here, particular pieces of information that are to be changed on RFID tag 908 are updated by RF generator 9. In one embodiment, every time the electrosurgical instrument is used, such usage is recorded on RFID tag 908. Such information may be the number of times the electrosurgical instrument is used, the type of usage, type of surgery, power settings etc. In this way, a particular electrosurgical instrument may only be permitted to be used a certain number of times. Such number of times may be a function of the types of surgical procedures undertaken by the electrosurgical instrument. For example, high power settings may be associated with fewer number of usages given increased wear or burnout during each usage.

Particular settings desired by a surgeon or used during surgery may be uploaded to RFID tag 908 such that the next time a surgeon uses a particular electrosurgical instrument, the settings used in the previous surgery in the RF generator 9 will be set for the current surgery.

Figure 12:
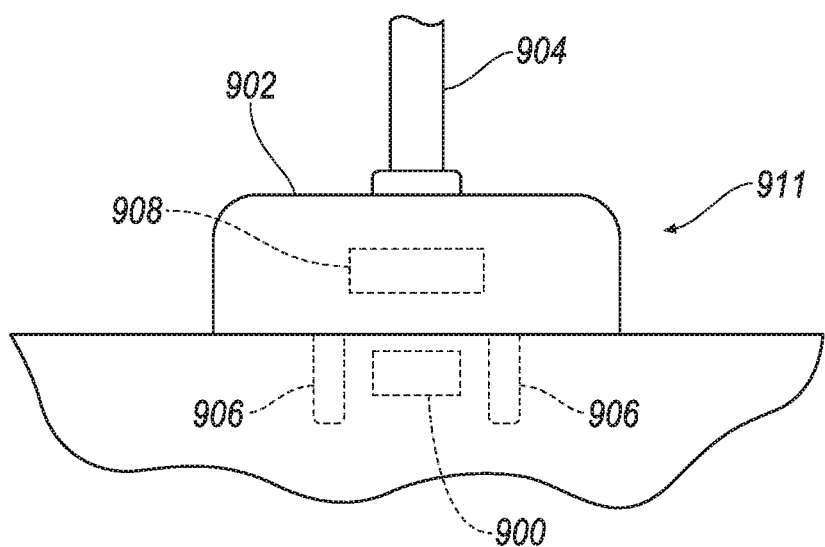
FIG. 12 illustrates a plan view of a RFID plug used in connection with an RF Generator for an Electrosurgical Instrument according to an aspect of the current invention.

Referring now to FIG. 12, plug 911 is shown plugged into any one of a monopolar plug 901 or bipolar plug 903 of RF generator 9. The plug is a plug designed to make electrical connection between the RF generator 9 and the associated electrosurgical instrument to provide RF current to the electrosurgical instrument. RFID tag 908 is located within the plug body 902 to make an RF connection to a RFID read and write device 900 that is located on the RF generator 9. In one example, the RFID reader and writer 900 is positioned just below the surface of the monopolar plug 901 or the bipolar plug 903. In this way, it is proximate the RFID tag 908 when plugged in.

Figure 13:
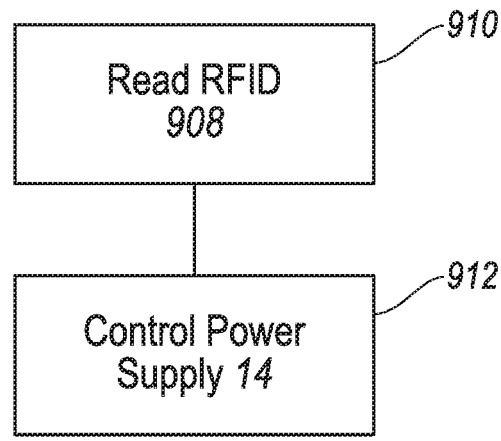
FIG. 13 illustrates a flowchart for processing in an RF Generator for an Electrosurgical Instrument according to an aspect of the current invention.
Figure 14:
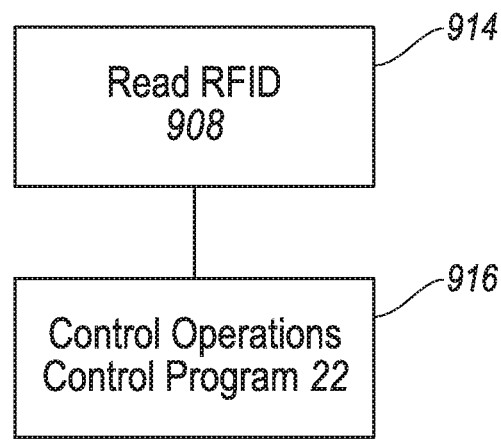
FIG. 14 illustrates a flowchart for processing in an RF Generator for an Electrosurgical Instrument according to an aspect of the current invention.

Referring now to FIG. 13, one operation according to an aspect of the present invention is shown and described. In FIG. 13, the process begins at step 910 where RFID tag 908 is read by RFID reader and writer 900. As described above, information such as the type of surgical equipment, surgical specialty, number of usages of the surgical equipment or other information (including that discussed above) may be read from RFID tag 908. In step 912, the information read from RFID tag 908 is passed to control power supply 14. Based on the information read from RFID tag 908, power settings of power supply 14 are altered, activated, stopped or changed depending on the information read. In one example, if the surgical instrument is a monopolar electrosurgical device plugged into a bipolar outlet (or vice versa), power supply 14 will not provide power to the monopolar electrosurgical instrument 58 or bipolar electrosurgical instrument 68. In another example, if the information read from RFID tag 908 is of a particular surgical type (for example OB/GYN) requiring a delicate or specific set amount of power, then power supply 14 will only provide a desired output power for the surgical procedure. Instead of providing the information to power supply 14, the information may instead be passed to operations control program 22 which includes the requisite logic required to control the power supply 14. In this way, no firmware or intelligence needs to be provided in power supply 14 and, instead, operations control program 22 handles all of the required logic for setting the power supply as shown in step 914 and 916 of FIG. 14.

Figure 15:
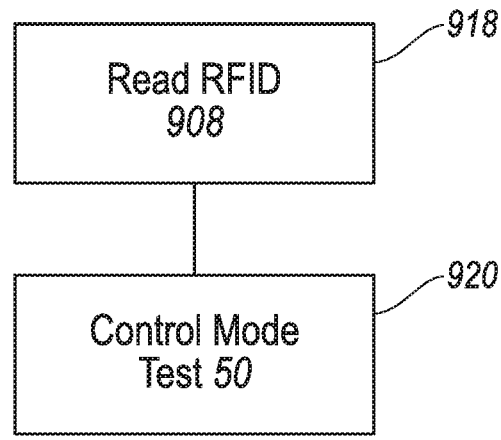
FIG. 15 illustrates a flowchart for processing in an RF Generator for an Electrosurgical Instrument according to an aspect of the current invention.

Referring now to FIG. 15, RFID tag 908 is read and step 918. In step 920, control mode test 50 receives the information from RFID tag 908. In response thereto, power may be routed to either monopolar transformer 54 or bipolar transformer 64 depending on the information received from RFID tag 908. For example, this RFID tag 908 indicates that a bipolar electrosurgical instrument is plugged in, mode test 50 may route power to bipolar transformer 64 and not monopolar transformer 54.

Figure 16:
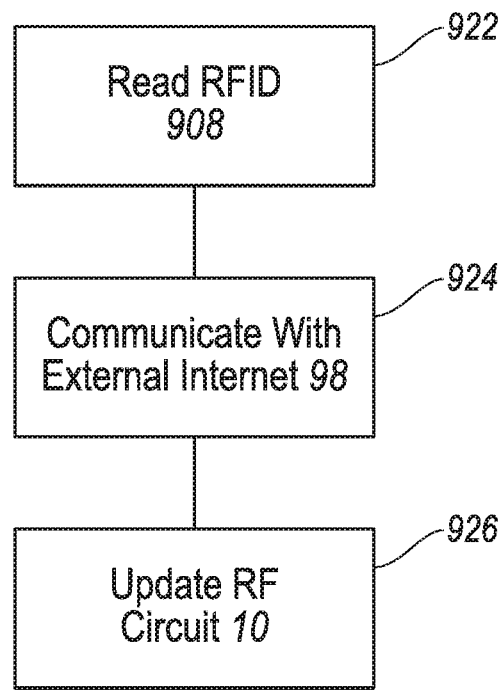
FIG. 16 illustrates a flowchart for processing in an RF Generator for an Electrosurgical Instrument according to an aspect of the current invention.

Referring now to FIG. 16, RFID tag 908 is read and step 922 the information from RFID tag 908 is then compared with information retrieved from external internet 98 in step 924. Updates to RF circuit 10 are then made based on information retrieved from the external internet 98. For example, updates or new versions may be downloaded circuit 10 such as updates to operations control program 22 based on the information stored on RFID tag 908. In one example, a new electrosurgical instrument may require specific settings in circuit 10 such as a specific operations control program. Based on the RFID tag 908, that update or new version for that specific electrosurgical instrument can be downloaded to circuit 10.

Figure 17:
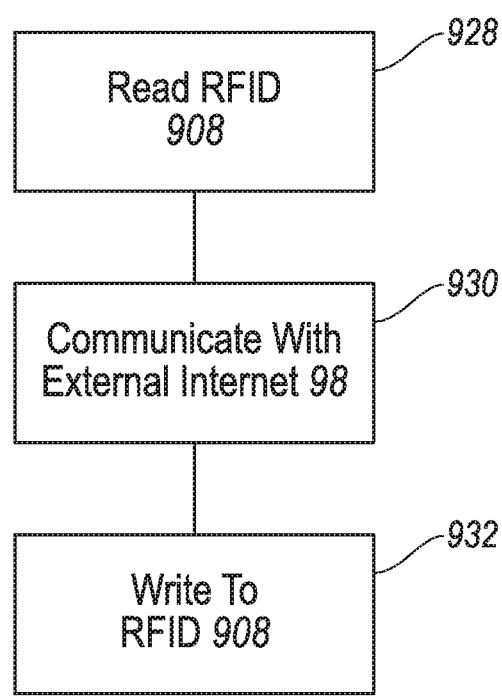
FIG. 17 illustrates a flowchart for processing in an RF Generator for an Electrosurgical Instrument according to an aspect of the current invention.

Referring now to FIG. 17, RFID tag 908 is read in step 928. In step 930, RFID reader and writer 900 communicates information read from RFID tag 908 with external internet 98. The information from RFID tag 908, such as for example make or model number of the electrosurgical instrument or other characteristics, is compared with information provided by external internet 98 to see if there are updates or other information that needs to be written to RFID tag 908. If so, then RFID reader and writer 900 writes the information to RFID tag 908.

In this specification, various preferred embodiments may have been described with reference to the accompanying drawings. It will, however, be evident that various modifications and changes may be made thereto, and additional embodiments may be implemented without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments have been chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than what is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A device for generating RF power for an electrosurgical instrument, said device comprising:
a power supply;
a circuit that generates electrosurgical current for the electrosurgical instrument, wherein the circuit is programmed to provide the electrosurgical current according to a specified set of predefined parameters, the circuit comprising a waveform generation module that outputs a waveform that is an AC signal,
wherein the waveform is amplified with a first amplification, an output of the first amplification being provided as a gate voltage to a gate bias for a power MOSFET thereby gating a voltage provided by the power supply such that the output of the first amplification is amplified to the voltage of the power supply;
a housing encapsulating the circuit, wherein the housing has at least one plug receptacle electrically connected to the circuit and defining a plug receptacle surface, wherein the plug receptacle includes a predetermined prong configuration and includes a read and write RFID positioned proximate the plug receptacle surface and internal of the housing, and;
wherein the electrosurgical instrument has a plug with a predefined prong configuration that is configured to mate with the predetermined prong configuration of at least one of the plug receptacles so that the plug electrically connects to at least one of the plug receptacles in the housing, wherein the plug further includes:
an RFID tag encoded with information thereon;
a base portion in which the RFID tag is located, wherein the RFID tag is positioned proximate and in communication with the read and write RFID when the plug is in electrical connection with the plug receptacle;
and
wherein the read and write RFID communicates with the RFID when the plug is connected to the plug receptacle; and
wherein the circuit changes the parameters based on the information.

2. The device of claim 1, further comprising:
wherein the information is a number of times the electrosurgical instrument has been used in a surgery; and
the power supply of the circuit ceases providing power to the electrosurgical instrument after the electrosurgical instrument has been used a predetermined number of times.

3. The device of claim 1, wherein the information is a type of surgical procedure for which the electrosurgical instrument is designed.

4. The device of claim 1, wherein the parameters are a member of a set consisting of power level, mode, monopolar setting, or bipolar setting.

5. The device of claim 1, further comprising:
an external internet connection connected to the read and write RFID;
wherein the read and write RFID receives update information from the external internet connection regarding the electrosurgical instrument; and
wherein the read and write RFID writes the update information to the RFID tag.

6. The device of claim 1, further comprising:
wherein the information is whether the electrosurgical device is permitted to be used with the circuit; and
wherein the power supply does not provide power to the electrosurgical instrument if the electrosurgical device is not permitted to be used with the circuit.

7. The device of claim 6, wherein:
the RFID tag includes an encrypted license number;

wherein the circuit contains a lookup table of approved license numbers; and wherein the power supply does not provide power to the electrosurgical instrument if the license number in the RFID tag is not found in the lookup table.

8. The device of claim 6, further comprising:
a GPS location component in the circuit that provides a location of the circuit;
a lookup table including a listing of approved locations stored in the circuit;
wherein the power supply does not provide power to the electrosurgical instrument if the circuit is located in a location other than the approved locations.

9. The device of claim 8, further comprising:
an Internet connection component in the circuit; and
wherein the lookup table is updated with update information from the Internet connection.

10. The device of claim 9, wherein a plurality of SUB ON and SUB OFF states creating the sub-discrete packets has a frequency between 3 kHz and 19 kHz.

11. The device of claim 10, wherein a plurality of second level SUB ON and second level SUB OFF states creating the second level sub-discrete packets has a frequency of 2 MHz.

12. The device of claim 11, wherein the power of the electrical signal to the electrosurgical instrument is in a range of between 40 and 200 watts.

13. The device of claim 1, the electrosurgical instrument further comprising:
at least one sensing device disposed within said electrical instrument, said sensing device configured to collect electrical power usage signals from the electrical instrument that represents an amount of power being distributed to an operative field by the electrosurgical instrument; and
a feedback circuit in electrical connection with the sensing device to receive electrical power usage signals and adjusting the output signal to the electrosurgical instrument to keep the amount of power at the operative field substantially constant.

14. The circuitry of claim 13, wherein the sensing device measures an impedance in the electrical instrument and wherein the feedback circuit comprises an algorithm utilizing the impedance to adjust the voltage supply input to an amplifier.

15. The circuitry of claim 13, wherein the sensing device measures voltage and current and wherein the feedback circuit comprises an algorithm utilizing a reading from the voltage and current to adjust the voltage supply input to an amplifier.

16. The circuitry of claim 9, wherein the electrosurgical instrument comprises a monopolar handpiece.

17. The circuitry of claim 9, wherein the electrosurgical instrument comprises a bipolar handpiece.

18. The circuitry of claim 1, wherein a discrete packets of the waveform are formed within a modulation envelope said modulation envelope having a shape of one of a group of rectangular, triangular, saw tooth, non-uniform, stair-step, ascending, descending and oval.

19. The circuitry of claim 13, wherein the sensing device is a temperature sensor and wherein the feedback circuit comprises an algorithm utilizing a reading from the temperature sensor to adjust the voltage supply input to an amplifier.

20. A device for generating RF power for an electrosurgical instrument, said device comprising:
a power supply;
a circuit that generates electrosurgical current for the electrosurgical instrument, wherein the circuit includes:
a GPS location component therein that provides a location of the circuit, and
a lookup table including a listing of approved locations stored in the circuit;
wherein the circuit is programmed to provide the electrosurgical current according to a specified set of pre-defined parameters, the circuit comprising a waveform generation module that outputs a waveform that is an AC signal;
wherein the waveform is amplified with a first amplification, an output of the first amplification being provided as a gate voltage to a gate bias for a power MOSFET thereby gating a voltage provided by the power supply such that the output of the first amplification is amplified to the voltage of the power supply;
a housing encapsulating the circuit, wherein the housing has a plug receptacle electrically connected to the circuit, wherein the plug receptacle includes a read and write RFID positioned proximate a surface of the housing, and;
wherein the electrosurgical instrument has a plug that electrically connects to the plug receptacle in the housing, wherein the plug further includes:
an RFID tag containing information concerning the electrosurgical instrument;
wherein the RFID tag is positioned proximate and in communication with the read and write RFID when the plug is in electrical connection with the plug receptacle; and
wherein the read and write RFID communicates with the RFID when the plug is connected to the plug receptacle; and
wherein the circuit changes the parameters based on the information, and
wherein the power supply does not provide power to the electrosurgical instrument if the circuit is located in a location other than the approved locations.

* * * * *